(12) United States Patent
Rock

(10) Patent No.: US 6,234,459 B1
(45) Date of Patent: May 22, 2001

(54) MEDICATION PROCESSING SYSTEM AND METHOD

(75) Inventor: Kelly Rock, Orlando, FL (US)

(73) Assignee: LyteSyde, LLC, Orlando, FL (US)

( * ) Notice: Subject to any disclaimer, the term of this patent is extended or adjusted under 35 U.S.C. 154(b) by 0 days.

(21) Appl. No.: 09/266,684

(22) Filed: Mar. 11, 1999

Related U.S. Application Data

(63) Continuation-in-part of application No. 09/040,666, filed on Mar. 18, 1998, now Pat. No. 6,113,078.

(51) Int. Cl.$^7$ .......................................................... B01F 3/04
(52) U.S. Cl. ........................... 261/79.2; 128/203.12; 261/DIG. 65
(58) Field of Search .................................. 261/78.2, 79.2, 261/78.1, 21, 79.1, 22, DIG. 65; 128/203.12

(56) References Cited

U.S. PATENT DOCUMENTS

| | | | |
|---|---|---|---|
| 3,506,589 | * 4/1970 | Hoffman et al. | 261/78.2 X |
| 3,515,676 | * 6/1970 | Hierta et al. | 261/78.2 X |
| 3,733,060 | 5/1973 | Merritt | 261/30 X |
| 3,761,065 | * 9/1973 | Rich et al. | 261/79.2 X |
| 3,811,278 | * 5/1974 | Taylor et al. | 261/79.2 X |
| 4,255,410 | * 3/1981 | Spevack | 261/79.2 X |
| 4,261,354 | 4/1981 | Nelson | 128/203.23 |
| 4,335,804 | * 6/1982 | Bardin et al. | 2261/78.2 X |
| 4,452,239 | 6/1984 | Malem | 128/200.17 |
| 4,568,500 | 2/1986 | Rock et al. | 261/DIG. 19 |
| 4,635,857 | * 1/1987 | Hughes | 261/78.2 X |
| 4,992,206 | * 2/1991 | Waldron | 261/78.2 X |
| 5,008,048 | * 4/1991 | Ryder | 261/78.2 |
| 5,476,093 | 12/1995 | Lankinen | 128/203.158 |
| 5,487,378 | 1/1996 | Robertson et al. | 128/200.16 |
| 5,512,216 | 4/1996 | Rock et al. | 261/79.1 X |
| 5,529,059 | 6/1996 | Armstrong et al. | 128/203.12 |
| 5,672,187 | 9/1997 | Rock et al. | 261/79.1 X |
| 5,687,710 | 11/1997 | Ambrosio et al. | 128/203.15 |
| 5,775,320 | 7/1998 | Patton et al. | 128/200.14 |
| 6,113,078 | * 9/2000 | Rock | 261/21 |

OTHER PUBLICATIONS

Translation of Russian Patent 5122773, dated Jun. 1976.

\* cited by examiner

*Primary Examiner*—Richard L. Chiesa
(74) *Attorney, Agent, or Firm*—Foster & Foster

(57) ABSTRACT

This disclosure relates to a centrifugal vortex system for preparing a liquid, such as medicine, and includes a chamber housing defining a vortex chamber. An array of tangential apertures are formed in the chamber housing to permit fluid to be turbulently introduced into the vortex chamber to create a vortical flow of fluid through the vortex chamber. In one embodiment, a plurality of vortex chambers are arranged in series to allow the fluid to pass through several vortex chambers. In other embodiments, the chamber housing may be stepped, textured, or both to increase the turbulence of the flow through the chamber. This present invention may be used for nebulizing and vaporizing fluids, powders and liquids for inhalation by a patient.

17 Claims, 17 Drawing Sheets

Figure 1:
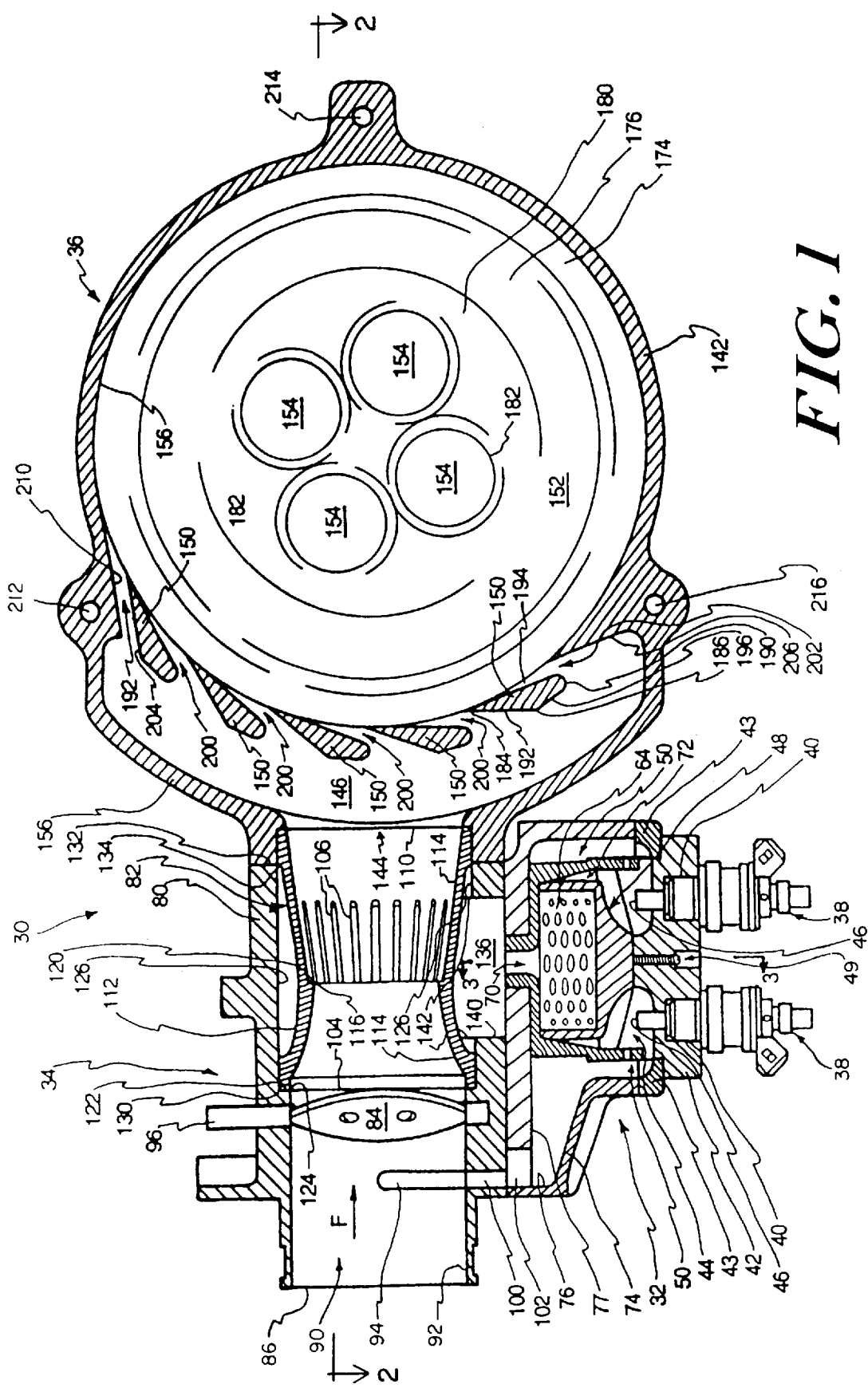

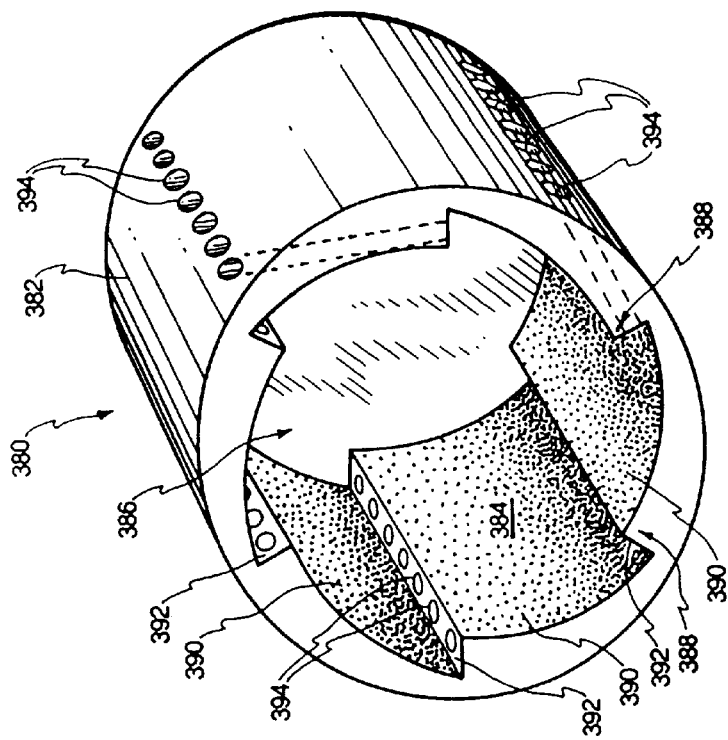
FIG. 14
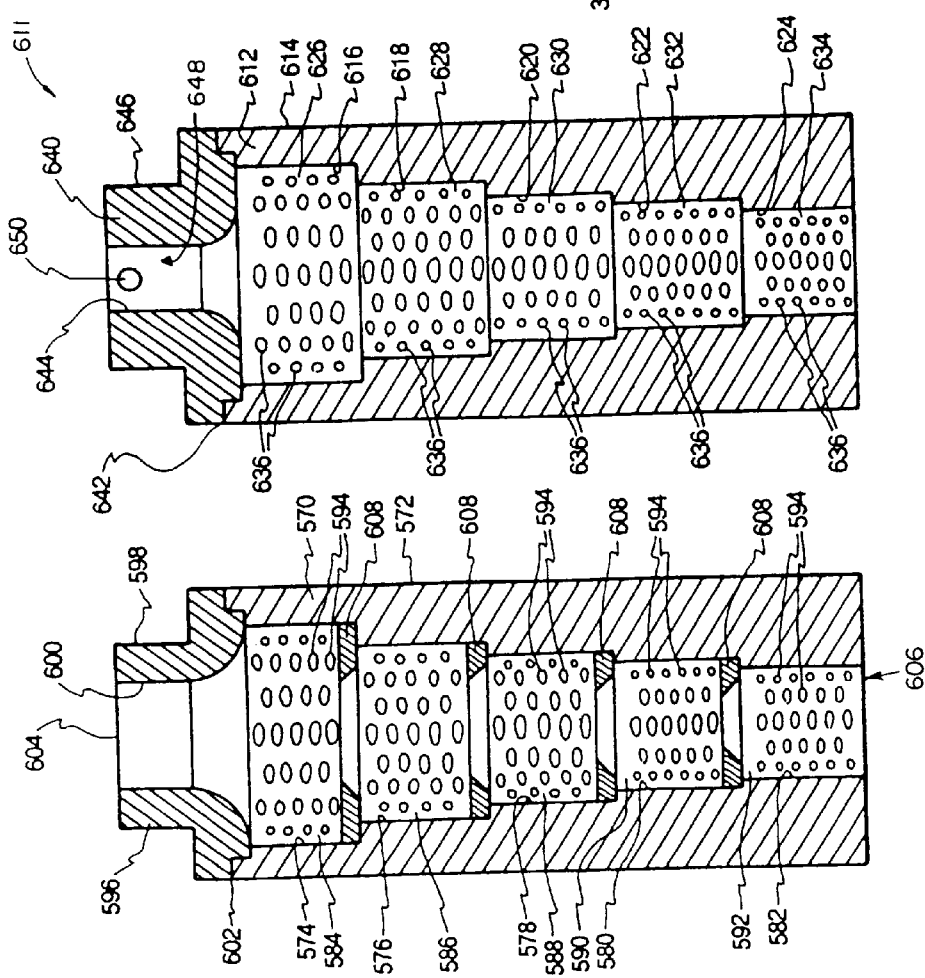
FIG. 16
FIG. 15

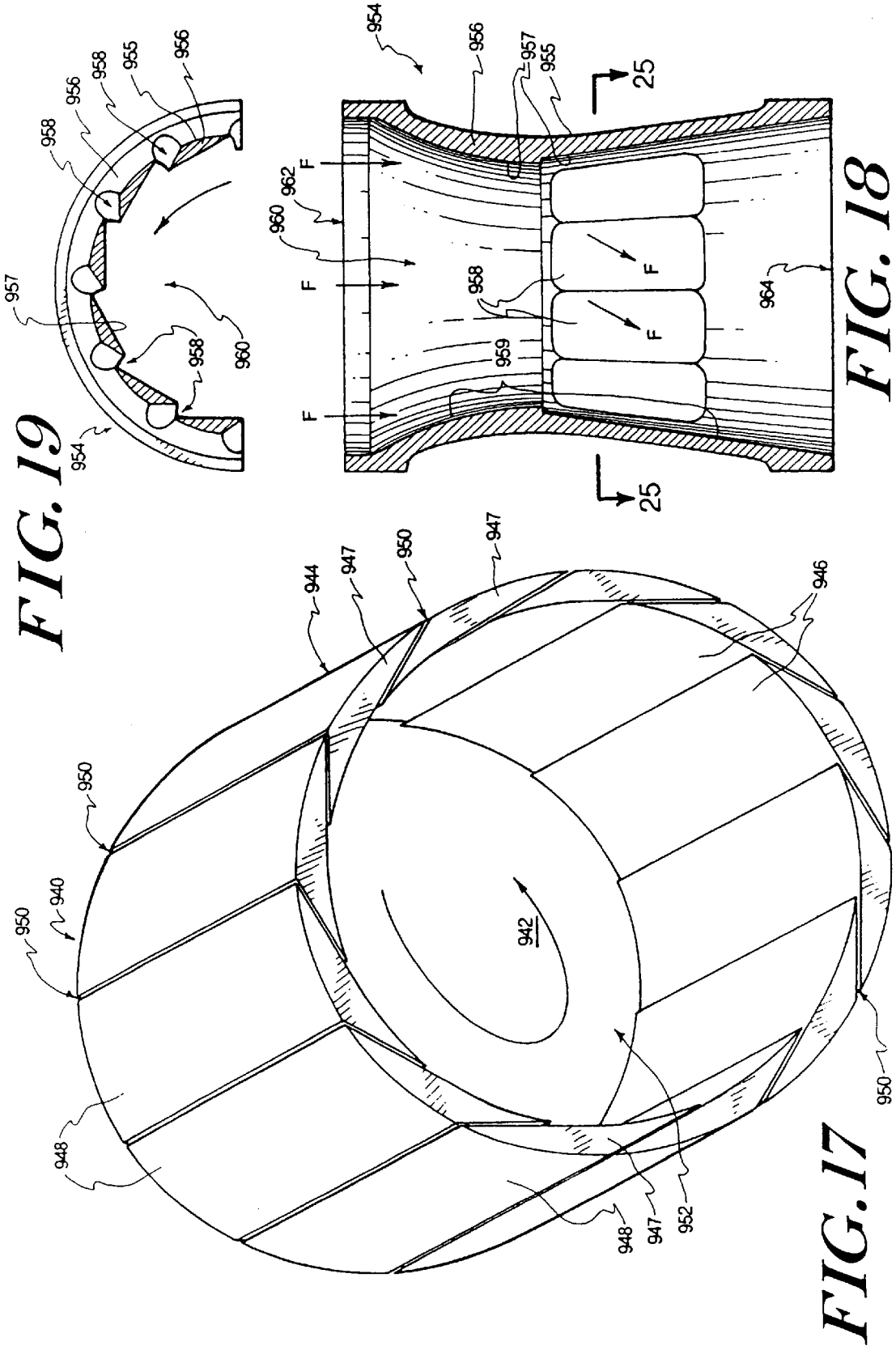

MEDICATION PROCESSING SYSTEM AND METHOD

RELATED APPLICATION

The present application is a Continuation-in-Part of U.S. patent application Ser. No. 09/040,666 entitled "FLUID PROCESSING SYSTEM AND METHOD" which was filed on Mar. 18, 1998, now U.S. Pat. No. 6,113,078, and which is incorporated herein by reference.

TECHNICAL FIELD

This invention relates to fluid vaporizing and homogenizing devices, to systems for vaporizing and homogenizing fluids, and more particularly to medical devices and systems for producing finely homogenized or vaporized gas-phase fluid mixtures.

BACKGROUND OF THE INVENTION

Many types of devices have been developed over the years for the purpose of converting liquids or aerosols into gas-phase fluids. Many such devices have been developed to prepare fuel for use in internal combustion engines. To optimize fuel oxidation within an engine's combustion chamber, the fuel/air mixture commonly must be further vaporized or homogenized to achieve a chemically-stoichiometric gas-phase mixture. Ideal fuel oxidation results in more complete combustion and lower pollution.

More specifically, relative to internal combustion engines, stoichiometricity is a condition where the amount of oxygen required to completely burn a given amount of fuel is supplied in a homogeneous mixture resulting in optimally correct combustion with no residues remaining from incomplete or inefficient oxidation. Ideally, the fuel should be completely vaporized, intermixed with air, and homogenized prior to entering the combustion chamber for proper oxidation. Non-vaporized fuel droplets generally do not ignite and combust completely in conventional internal and external combustion engines, which presents problems relating to fuel efficiency and pollution.

Another problem, different from applications of vortex technology to internal combustion engines, relates to the extreme vaporization needed for various medications administered via inhalers. An inhaler typically produces a liquid/gas mixture of the medication for inhaling directly into the lungs. Problems have arisen, however, in that the high degree of vaporization required for directly passing the medication through the lungs into the bloodstream has been difficult to achieve. That is, excess amounts of the medication remain liquefied, rather than being further broken down into smaller molecular size particles, for passing immediately through the lungs into the bloodstream. A need exists, therefore, to develop certain vaporization devices that will further vaporize and homogenize liquid/gas mixtures into a vapor of sufficiently small vapor particles for administering medication directly into the bloodstream via the lungs.

Prior art devices have employed vortex chambers wherein fluid is introduced into a gas passing through a cylindrical chamber with a vortex action. These vortex chambers have smooth, cylindrical inner walls. A smooth vortex chamber inner wall construction may limit the degree of turbulence within a given chamber and the effective rate of vaporization within the vortex chambers.

Another perceived shortcoming of prior devices is their inability to compensate for differential pressures at the various inlets leading to the vortex chamber. As the gas/fluid mixture passes through the various vortex chambers, additional gas is tangentially added in each chamber which causes a pressure differential at the various inlets. By supplying ambient air at all of these inlets to the vortex chamber, it has been difficult to maintain an optimal gas-to-fluid ratio as the mixture passes through the vortex chambers.

Yet another aspect of the pressure differential problem associated with prior known devices is that there is a tendency for the vortex chambers positioned closer to the low pressure end of the flow path (for example, closer to the engine manifold) to dominate the other vortex chambers by receiving substantially more flow. This tendency is particularly noticeable and problematic during periods of engine acceleration. As the vortex chambers closer to low pressure end of the flow path dominate the other vortex chambers, the effectiveness of the other vortex chambers is significantly reduced.

The prior centrifuge vaporization devices also have certain limitations, such as being too voluminous, failing to effectively introduce fluid into the centrifuge chamber tangentially, unnecessarily inhibiting the drawing power of the engine manifold vacuum, and unevenly discharging the centrifuge contents into the engine manifold.

Yet another problem concerning prior cyclone vaporization devices is that they have failed to appreciate or utilize the advantages associated with adjustable vortex chamber output ports and adjacent chambers of different diameters.

In view of the foregoing, there is a need to develop a centrifugal vortex system that solves or substantially alleviates the above-discussed limitations associated with known prior devices. There is a need to develop a centrifugal vortex system with a vortex chamber that enables a more optimal turbulent flow, that more completely breaks down liquid into smaller sized particles of vapor fluid, and that normalizes the flow through the various apertures formed in the vortex chamber housing. There is a further need to provide a centrifugal vortex system that more optimally premixes air and fuel prior to introducing the air/fuel mixture into the vortex chamber. Another need exists to provide a low-volume centrifuge apparatus that more optimally mixes, vaporizes, homogenizes, and discharges more minutely sized molecular vapor particles into an engine manifold, from an inhaler-type medicinal administration device, and to/from other desired applications.

SUMMARY OF THE INVENTION

It is an object of the invention to provide a vortex chamber that enables a more optimal turbulent flow and which substantially eliminates the formation of liquid orbital rings on the inner walls within the vortex chamber.

Another object of the invention is to provide a vortex chamber housing with a stepped inner wall surface for increasing the turbulence of fluid flowing through the vortex chamber.

Another object of the invention is to provide a vortex chamber housing with an irregular or textured inner wall surface for increasing the turbulence of fluid flowing through the vortex chamber.

Another object of the invention is to provide a pressure differential supply, such as a tapered air-feed channel formed perhaps by a jacket, to equalize the amount of flow entering several input apertures formed in a vortex chamber.

Another object of the invention is to provide a series of tangentially oriented baffles associated with a centrifuge chamber to form a series of tangential passageways into the centrifuge chamber to enhance the centrifugal flow of fluid in the centrifuge chamber.

Another object of the invention is to increase turbulence within the vortex chamber by reducing the chamber volume and by employing a centrifuge vertical wall with a height less than the maximum inside diameter of an associated venturi.

Another object of the invention is to provide a more optimal turbulence within a vortex chamber and to achieve improved vaporization by causing a vortical flow to spin in alternative, opposite spin directions as the vortical flow passes from one vortex chamber to an adjacent vortex chamber.

Still another object of the present invention is to provide a device for breaking down a vapor/gaseous mixture into more minute sized particles on a molecular scale for medical applications. Still another object of the invention is to produce a device that allows a vapor/liquid mixture to be broken down into extremely small sized particles such that the particles pass immediately and directly through the lungs into a person's bloodstream.

In one embodiment, the inner wall of the vortex chamber housing is stepped or textured, or both, to enhance the turbulence of a flow through the vortex chamber. In another embodiment, several stages of vortex chambers are used.

In still another embodiment, a deceleration chamber is fluidly coupled to at least one vortex chamber, the deceleration chamber to allow the gas/fluid mixture to fully homogenize, and also allows for separation when the present invention is used for fluid separation, for example desalinization.

Other objects, features, and advantages of the invention will become apparent from the following detailed description of the invention with reference to the accompanying drawings.

BRIEF DESCRIPTION OF THE DRAWINGS

Preferred embodiments of the invention are described below with reference to the accompanying drawings:

FIG. 1 is a top sectional view of a centrifugal vortex system according to the present invention;

FIG. 2 is a side sectional view taken along line 2—2 of FIG. 1, of the centrifugal vortex system;

FIG. 3 is an enlarged breakaway sectional view of a portion of the vaporizing section of FIG. 1;

FIG. 4 is a top view of the injector plate of FIG. 1;

FIG. 5 is a sectional view taken along line 5—5 of FIG. 4 of the injector plate;

FIG. 6 is a bottom view of the injector plate of FIG. 1;

FIG. 7 is a sectional side view of an alternative embodiment of a vortex configuration according to the present invention;

FIG. 8 is a bottom sectional view taken along line 8—8 of FIG. 7 of the differential inlet supply configuration to a vortex chamber assembly;

FIG. 9 is a side sectional view taken along line 9—9 of FIG. 8 of the differential inlet supply configuration to a vortex housing assembly;

FIG. 10 is a top view of the differential inlet supply configuration to a vortex housing assembly of FIG. 8;

FIG. 11 is a bottom sectional view of an alternative embodiment of a differential inlet supply configuration to a vortex chamber assembly according to the present invention;

FIG. 12 is a side sectional view, taken along line 12—12 of FIG. 11, of the differential inlet supply configuration to a vortex chamber assembly;

FIG. 13 is a top view of the differential inlet supply configuration for the vortex chamber assembly of FIG. 11;

FIG. 14 is a perspective view of an alternative embodiment of a vortex chamber housing according to the present invention;

FIG. 15 is a sectional view of yet another alternative embodiment of a vortex housing according to the present invention;

FIG. 16 is a sectional view of still another alternative embodiment of a vortex chamber housing according to the present invention;

FIG. 17 is a perspective view of yet another alternative embodiment of a vortex chamber housing according to the present invention;

FIG. 18 is a sectional side elevation view of an alternative embodiment of a venturi according to the present invention;

FIG. 19 is a partial cross-sectional view, taken along the line 25—25 of FIG. 18, of an alternate embodiment of a venturi according to the present invention;

FIG. 20 is a sectional side elevation view of still another alternate embodiment of a centrifugal vortex system for vaporizing a fluid according to the present invention;

FIG. 21 is an enlarged sectional view of a portion of the embodiment illustrated in FIG. 20;

FIG. 22 is a sectional side elevation view of still another alternate embodiment of a multi-stage centrifugal vortex system for vaporizing a fluid according to the present invention;

FIG. 23 is a sectional side exploded view of still another alternate embodiment of a single-stage centrifugal vortex system for vaporizing a fluid according to the present invention;

FIG. 24 is a sectional side elevation view of still another alternate embodiment of a single-stage centrifugal vortex system for vaporizing a fluid according to the present invention;

FIG. 25A–C is a bottom, side, and top view of the input mixer of the embodiment illustrated in FIG. 24;

FIG. 26A–C is a bottom, side, and top view of the processor of the embodiment illustrated in FIG. 24; and FIG. 27A and B is a sectional side elevation view of alternate nozzles of the embodiment illustrated in FIG. 24.

DETAILED DESCRIPTION OF THE INVENTION

In the context of this document, the terms "homogenize" or "vaporize" or any derivative of these terms means to convert a liquid from an aerosol or vapor-phase to a gas-phase by vorticular turbulence where high velocity, low pressure, and high vacuum conditions exist, i.e., where differential pressures exist.

FIGS. 1–6 show a first embodiment of a centrifugal vortex system 30 according to the present invention. As shown in FIG. 1, the centrifugal vortex system 30 has three sections: a fuel vaporizing section 32, a main air section 34, and a centrifuge section 36. The fuel vaporizing section 32 is illustrated as having two fuel injectors 38 mounted in bores 40 formed in an injector plate 42. The fuel injectors 38 may comprise conventional electronic fuel injectors and preferably have a spray angle of about 30°.

A preliminary mixing chamber 44 is formed in the fuel vaporizing section 32, into which fuel is sprayed by the output ports 46 of the fuel injectors 38. Ambient air is also introduced into the preliminary mixing chamber 44 through an ambient air conduit 50 and is to be mixed with fuel sprayed by the fuel injectors 38. The preliminary mixing chamber 44 is defined in part by an exterior surface 52 of a vortex chamber housing 54 and the exterior surface 68 of a tapered extension 58. The preliminary mixing chamber 44 is further defined by the interior surface 56 of a pressure differential supply jacket 60. The purpose and function of the jacket 60 and the vortex chamber housing 54 are discussed in more detail below.

The vortex chamber housing 54 comprises the exterior surface 52, an inner chamber wall surface 62, and a bottom surface 63. Additionally, the vortex chamber housing 54 includes the tapered extension 58 to enhance the flow of fluid in the preliminary mixing chamber 44, and is to be secured to the injector plate 42 by set screw 48 (FIG. 3) inserted through bore 49. The vortex chamber inner chamber wall surface 62 defines a vortex chamber 64 in which a vortical flow of fluid is created. The vortex chamber housing 54 has an array of apertures 66 journalled into the housing at an angle to allow the input of fluid, such as an air/fuel mixture, tangentially into the vortex chamber 64. A vortex chamber top edge 61 abuts a jacket top inside surface 55. Advantageously, a conventional gasket (not shown) may be interposed between the edge 61 and the top surface 55 to prevent fluid from leaking into the vortex chamber 64 between the edge 61 and the surface 55.

Figure 3:
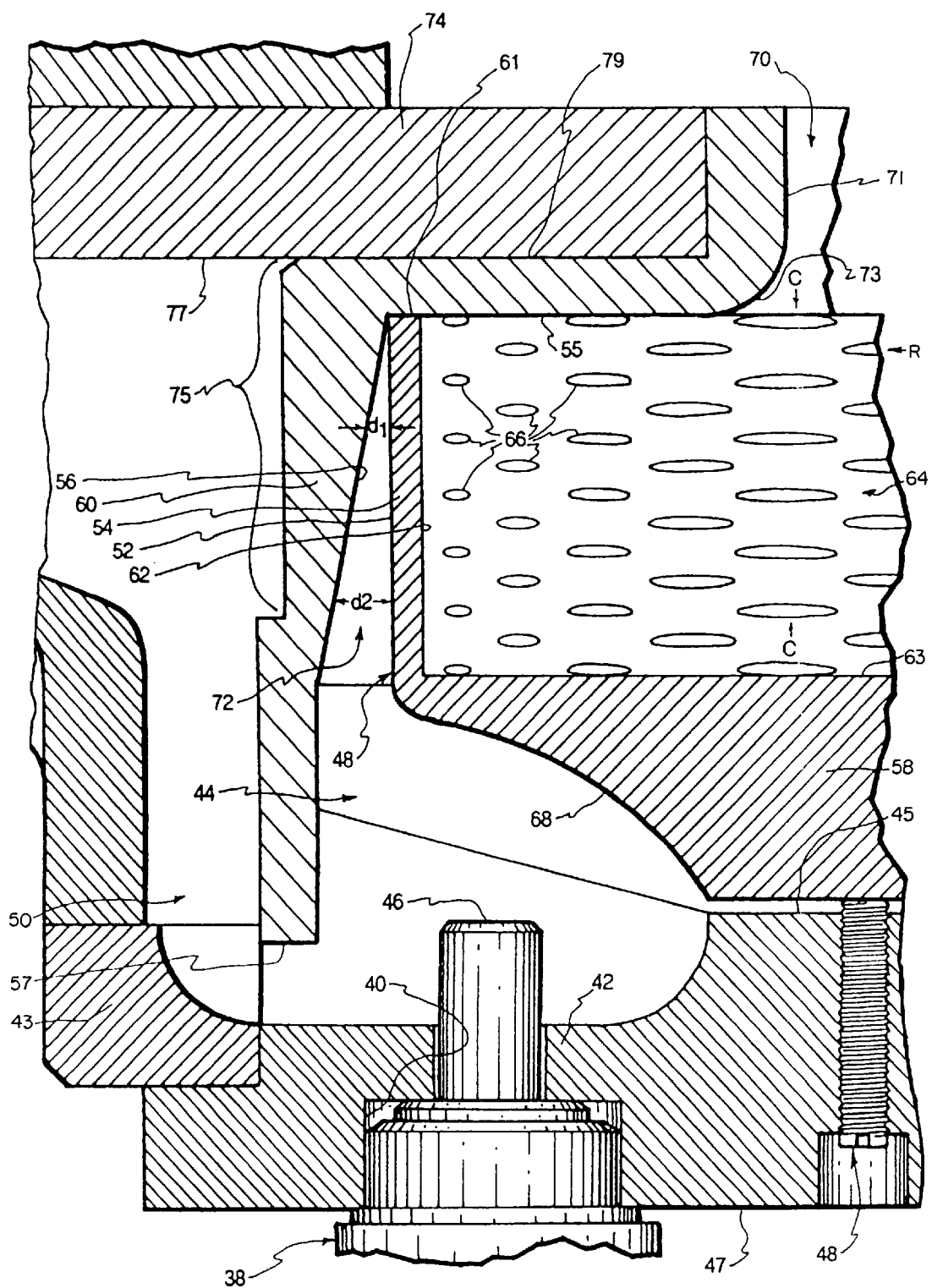

As shown in FIG. 3, the array of apertures 66 are arranged in a plurality of rows R and in a plurality of columns C about the vortex chamber 64 to enhance the turbulence of the vortical flow through the chamber 64. Preferably, the rows R and the columns C are circumferentially staggered or offset relative to each other. By orienting the array of apertures 66 in staggered rows and columns, the tendency for the fluid within the vortex chamber 64 to separate into discrete orbital rings is eliminated or at least substantially alleviated. Additionally, this aperture orientation significantly enhances the degree of turbulence (and thus the efficiency of vaporization) within a given vortex chamber.

A pressure differential supply configuration is formed by a tapered jacket 60 positioned around the vortex chamber housing 54. As shown, the jacket 60 includes a variable thickness portion 75 which provides an increasing diameter to the tapered inside surface 56. The jacket 60 terminates at edge 57. The jacket 60 also includes an output port 70 through which fluid flows after being processed in the vortex chamber 64. The output port 70 is defined by a cylindrical surface 71 which intersects the jacket top surface 55 at rounded corner 73. The diameter of the jacket interior surface 56 is illustrated as being smallest at the end closest to the jacket output port 70. The diameter of the jacket interior surface 56 gradually increases from that point toward the edge 57. While the variable diameter surface is illustrated as generally comprising the tapered inside surface 56, it is appreciated that a stepped inside surface may also be effectively employed.

The variable diameter jacket interior surface 56, when positioned around the vortex chamber housing 54, defines a variable width gap 72 between the jacket interior surface 56 and the vortex chamber housing exterior surface 52. As shown in FIG. 3, the variable width gap has a smaller width at $d_1$ and a larger width at $d_2$. The variable width gap 72 creates a variable pressure differential across the apertures 66 formed in the vortex chamber housing 54 and restricts the flow through the apertures 66 closer to the port 70 more than the apertures 66 located farther from the port 70. Thus, a differential pressure of fluid is provided at the various input apertures 66 according to the location of the apertures relative to the jacket output port 70. In operation, the apertures 66 closest to output port 70 will be provided with more pressure because this end comprises the lower pressure end of the fuel vaporizing section 32.

By positioning a variable pressure supply configuration, such as the jacket 60, around the apertures 66 formed in the chamber housing 54, the amount of fluid flow entering the various apertures 66 is substantially equalized. Having a substantially equalized flow of fluid through the various apertures 66 enhances the efficiency and effectiveness of the vortex chamber 64.

The jacket 60 and the vortex chamber housing 54 are illustrated in FIG. 1 as being mounted within a fuel vaporizing housing 74 having an interior surface 76. Specifically, a top outside surface 79 (FIG. 3) of the jacket 60 is positioned adjacent to a top inside surface 77 of the housing 74. The ambient air conduit 50, discussed above, is defined by the fuel vaporizing housing interior surface 76 and the exterior surface 68 of the tapered extension 58.

Figure 4:
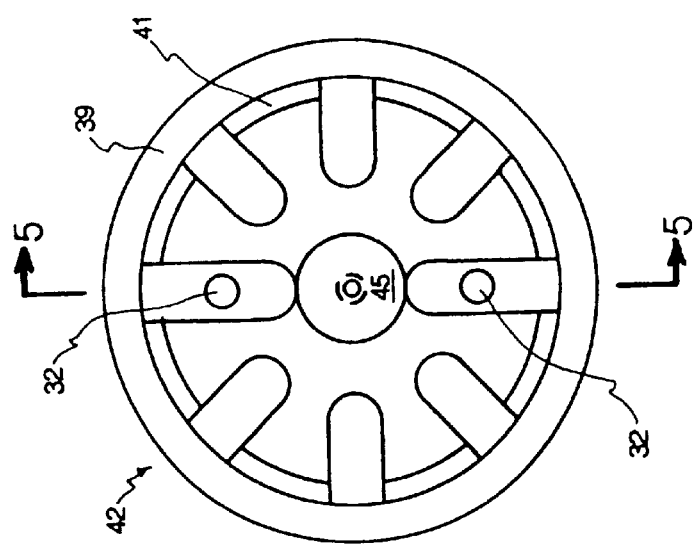
Figure 5:
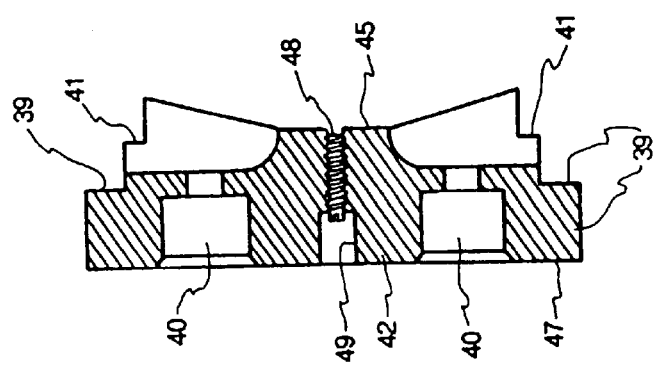
Figure 6:
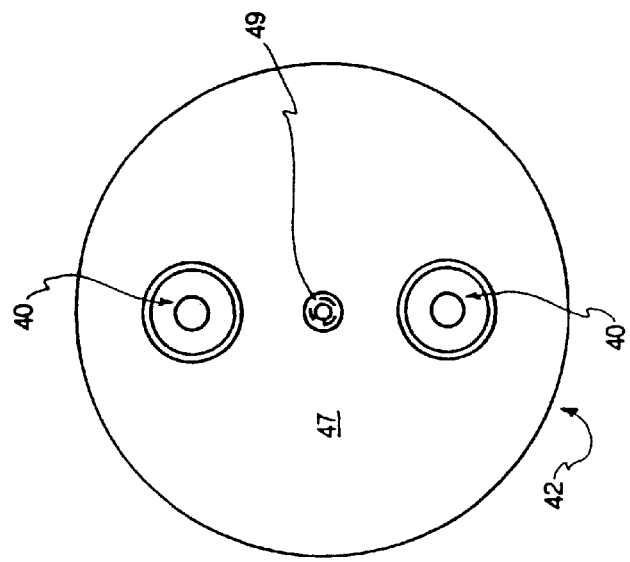

The injector plate 42 is shown in FIGS. 1, 3, 4, 5, and 6. The injector plate 42 includes a pair of bores 40 formed through the bottom surface 47 to receive the fuel injectors 38 (FIG. 1). The injector plate 42 further includes a first shoulder 39 and a second shoulder 41 (FIGS. 4 and 5). The first shoulder 39 abuts a connecting member 43 and the second shoulder 41 abuts the jacket edge 57 (FIG. 1). A cylindrical center extension 45 abuts and is connected to the tapered extension 58 (FIG. 1) via the set screw 48.

Figure 2:
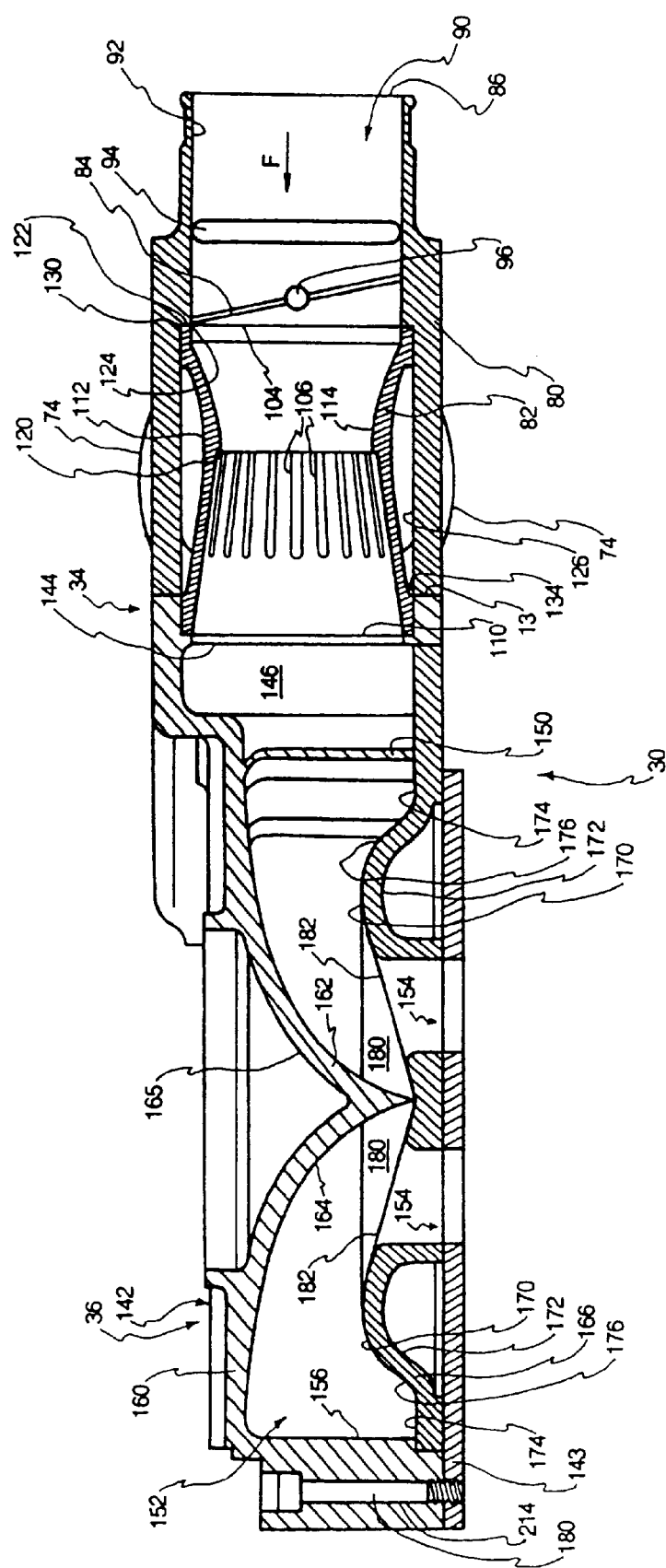

The main air section 34, as illustrated in FIGS. 1 and 2, comprises a main air housing 80, a venturi body 82, and a conventional butterfly throttle plate 84. An air intake opening 86 is positioned at one end of the main air section 34. The air intake opening 86 leads to an interior cylindrical portion 90 having an annular inside surface 92.

The conventional throttle plate 84 is pivotally secured within the interior cylindrical portion 90. The throttle plate 84 is secured to a rotatable central shaft 96, which is oriented transverse to the direction of air flow F through the hollow interior 90. Rotation of the shaft 96 will adjust an inclination angle of the throttle plate 84 within the hollow interior 90, thereby changing the volume of air and thus the air/fuel mixture admitted to the engine.

An ambient air channel 100 is formed in the main air intake housing 80. The air channel 100 is in fluid communication with a slot 94 formed in the main air intake housing 80. Sequential ambient air conduits 102 and 50 allow air to pass through the channel 100 and the slot 94 into the preliminary mixing chamber 44.

A venturi 82 is mounted within the main air section 34 and comprises an input 104, a plurality of elongated apertures 106, and a venturi output 110. Additionally, the venturi 82 includes a venturi exterior surface 112 and a venturi interior surface 114. As shown, the diameter of the venturi interior surface 114 is maximized at the venturi input 104 and at the venturi output 110. The diameter of the venturi interior surface 114 is approximately the same at the venturi input 104 and at the venturi output 110. In contrast, the diameter of the venturi interior surface 114 is minimized at the venturi throat 116. An annular step is formed on the venturi interior surface 114 adjacent to the venturi throat 116.

The main air intake section 34 also includes a transverse annular edge 122 (FIGS. 1 and 2) which intersects the annular inside surface 92 at an annular outside corner 124. The edge 122 also intersects an annular surface 126 at an annular inside corner 130. The annular surface 126 also intersects with a transverse edge 132 at an annular corner 134. The venturi 82 is positioned within the main air section adjacent to the annular surface 126 by securing the exterior surface 112 of the venturi 82 to the annular surface 126 by adhesion, by an interference fit, or by any other conventional manner.

An intermediate mixing chamber 136 (FIG. 1) is formed in the main air intake section 34 to cause a spinning column of fluid exiting the jacket output port 70 to enfold and to mix turbulently prior to entering the venturi 82 through the elongated apertures 106. The intermediate mixing chamber 136 serves to further vaporize and homogenize the fluid. The intermediate mixing chamber is defined by the annular surface 126 and the transverse annular surface 140 which intersect at corner 142. The centrifuge section 36 is attached to the main air section 34 at the transverse edge 132.

Fluid discharged from the venturi output 110 passes into the centrifuge section 36 through an intake opening 144. The centrifuge section 36 generally comprises a centrifuge housing 142, the intake opening 144, an entry chamber 146, a series of baffles 150 oriented tangentially relative to a centrifuge chamber 152, and a plurality of output passageways 154. As shown, the centrifuge housing is a generally cylindrical configuration comprising an annular vertically directed wall surface 156 which is interrupted by the intake opening 144. The wall surface 156 is formed integrally with a top wall 160 (FIG. 2).

As shown in FIG. 2, a hub portion 162 extends down from the centrifuge top wall 160. The hub portion 162 has an inner surface 164 and an exterior surface 165, both of which are shown as being substantially parabolic in shape. As discussed in further detail below, the hub portion 162 substantially reduces the volume of the centrifuge chamber 152 and enhances the circular, centrifugal flow of fluid about the hub portion within the centrifuge chamber 152.

Opposite the top wall 160, a contoured bottom insert 166 is positioned within the centrifuge chamber 152. The contoured bottom insert 166 comprises a contoured top surface 170 and a contoured bottom surface 172. The contoured top surface has an annular flat portion 174, an upward directed curved portion 176, and a conically shaped central portion 180. As shown, each output 154 includes an output opening 182 formed in the conically shaped portion 180.

As mentioned above, the centrifuge 136 also includes the series of tangentially oriented baffles 150 positioned within the entry chamber 146. Each baffle 150 comprises leading edge 184, and an intermediate corner 186 as well as a rounded trailing end 190. A leading flat surface 192 is formed between the leading edge 184 and the corner 186. A flat surface 194 is formed between the leading edge 184 and the trailing end 190. Lastly, a surface 196 is formed between the corner 186 and the trailing end 190.

The baffles 150 are aligned relative to one another so as to create a plurality of tangential fluid flow passageways 200 formed between the surfaces of adjacent baffles 150. Additionally, a tangential passageway 202 is formed between the surface 194 of a baffle 150 adjacent to the vertically oriented wall 206 of the entry chamber 146. Moreover, a tangential passageway 204 is formed between the surface 192 of a baffle adjacent to a vertical wall 210 of the entry chamber 146.

As shown in FIG. 1, each trailing flat surface 194 is oriented at a tangential angle relative to the annular wall 156 of the centrifuge section 36. Accordingly, the flow of fluid introduced into the centrifuge chamber 152 through the passageways 200, 202, and 204 is introduced in a direction substantially tangent to the annular wall 156 to enhance the circular and centrifugal flow of fluid in the chamber 152.

To secure the centrifuge housing 142 to an engine manifold (not shown), mounting locations 212, 214, and 216 are formed in the centrifuge housing to permit fasteners, such as bolts 180 (FIG. 2) to secure the centrifuge housing 142 to the engine via an interface plate 143.

Figure 7:
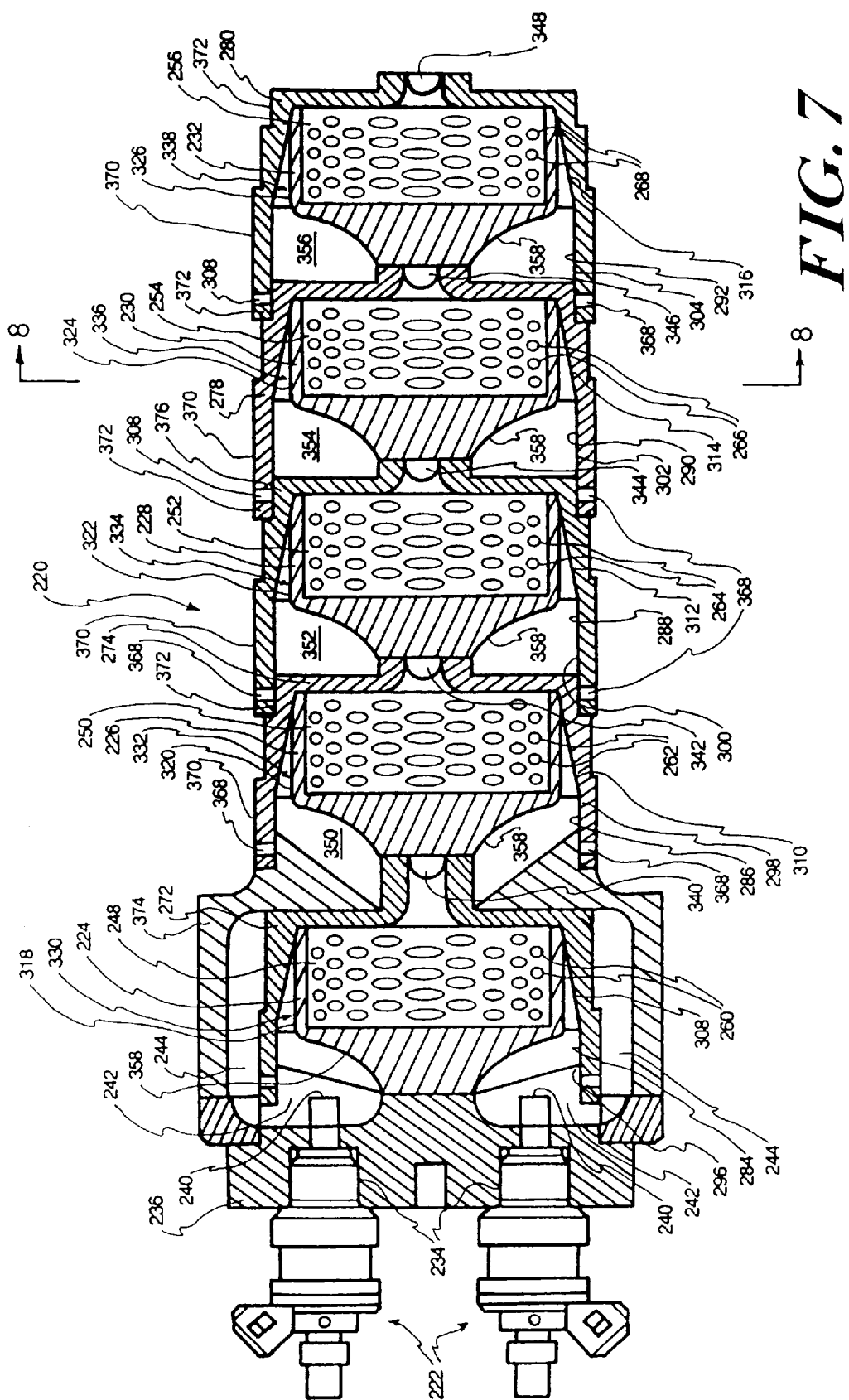

FIG. 7 illustrates an alternative embodiment of the present invention. This embodiment shows a vortex chamber assembly 220 which generally comprises conventional electronic fuel injectors 222, a first vortex chamber housing 224, and subsequent vortex chamber housings 226, 228, 230, and 232. In this configuration, the chamber housings 226–232 each receive a flow of fluid exclusively from the preceding chamber housing. For example, the chamber housing 228 receives fluid exclusively from the output of chamber housing 226 and so on.

The fuel injectors 222 are mounted within bores 234 formed in an injector plate 236. Each fuel injector includes an output port 240 which sprays fuel into a preliminary mixing chamber 242. Ambient air is introduced into the preliminary mixing chamber 242 via an ambient air conduit 244. The preliminary mixing chamber 242 and the ambient air conduit 244 are configured and function in a manner similar to the configuration and function of the preliminary mixing chamber 44 and the ambient air conduit 50 illustrated in FIG. 1.

The chamber housings 224, 226, 228, 230, and 232 respectively define vortex chambers 248, 250, 252, 254, and 256. The vortex chambers 224–232 each have an array of apertures 260–268. Each array of apertures 260–268 are arranged in a plurality of rows and a plurality of columns in a manner similar to that illustrated in FIG. 3. Moreover, each array of apertures 260–268 are arranged in a staggered configuration so as to enhance the turbulence of a vertical flow through the respective vortex chamber 248–256.

Pressure differential supply inlets are formed by tapered jackets 272, 274, 276, 278, and 280 positioned about the chamber housings 224, 226, 228, 230, and 232, respectively. Each functions in a manner similar to the jacket 60 described in connection with FIG. 1. Each of the jackets 272–280 has a respective interior surface 284, 286, 288, 290, 292. The jacket interior surfaces 284–292 each comprises a constant diameter portion 296, 298, 300, 302, 304, respectively, and a variable diameter interior surface portion 308, 310, 312, 314, 316, respectively. Each chamber housing 224, 226, 228, 230, 232 has a respective exterior surface portion 318, 320, 322, 324, 326. The jackets form variably sized gaps 330, 332, 334, 336, 338 between the surfaces 330–338 and the surfaces 308–316, respectively. As such, the variable spaced gaps allow a differential pressure of fluid at the various apertures 260–268 according to the location of the apertures 260–268 and function in a manner similar to the gap 72 (FIGS. 1 and 2).

Figure 10:
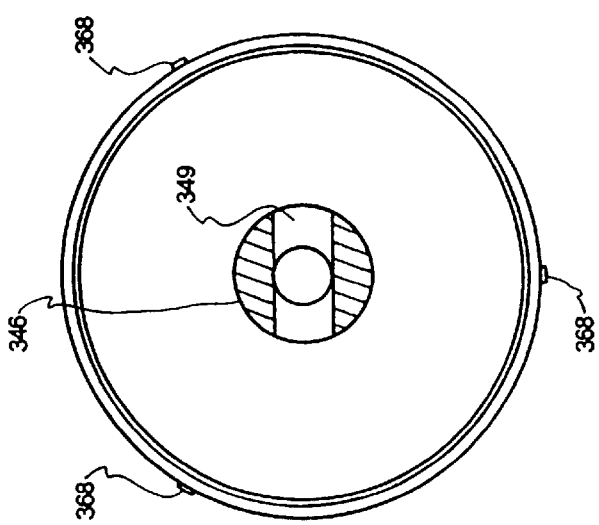
Figure 9:
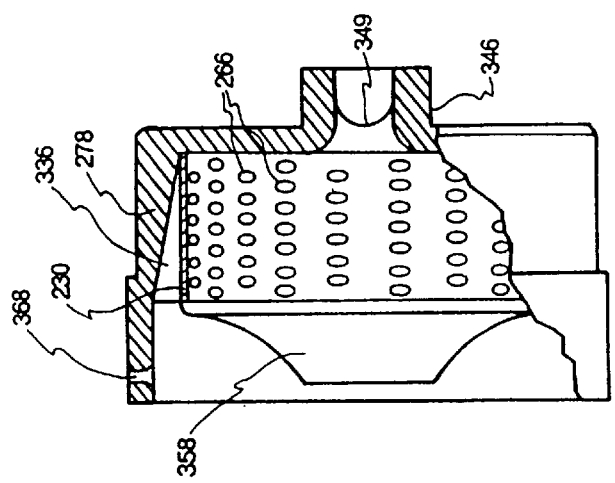
Figure 8:
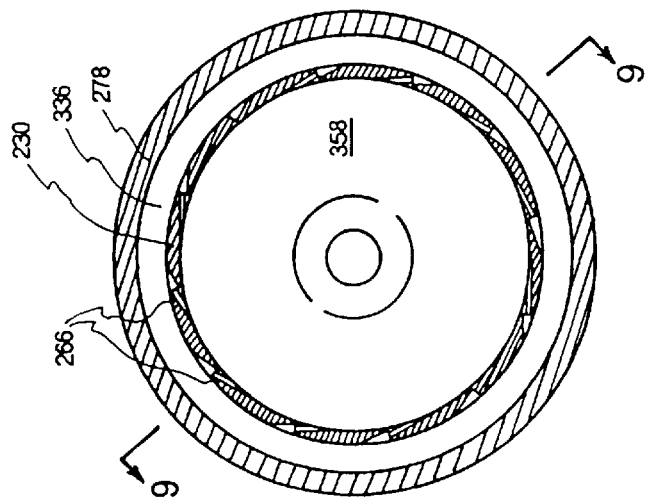

Additionally, each jacket 272–280 has a respective output port 340–348 which is in fluid communication with the subsequent vortex chamber. FIGS. 8–10 illustrate the jacket 278 vortex chamber 254 in greater detail. Each of the output ports 340–348 is in the form of a U-shaped slot represented by reference numeral 349 in FIGS. 9 and 10. The output ports 340–346 are in fluid communication with subsequent mixing chambers 350, 352, 354, and 356, respectively, so that the apertures 262–268 receive a fluid mixture exclusively from the output ports 340–346 to maintain a substantially constant air second fluid mixture as no additional air is introduced into the fluid stream as the fluid stream passes through the vortex chambers 250–256. Moreover, to enhance the mixing and vortical nature of the flow through the mixing chambers 242, 350, 352, 254, and 356, each chamber housing 224–232 has a conically tapered base portion 358.

Apertures 368 are formed in the jackets 274–280 for receiving fasteners (not shown), such as conventional set screws, to secure the jacket lower portions 370 to a preceding jacket's upper portion 372 or to a vaporizing housing 374.

Figures 11, 12, 13:
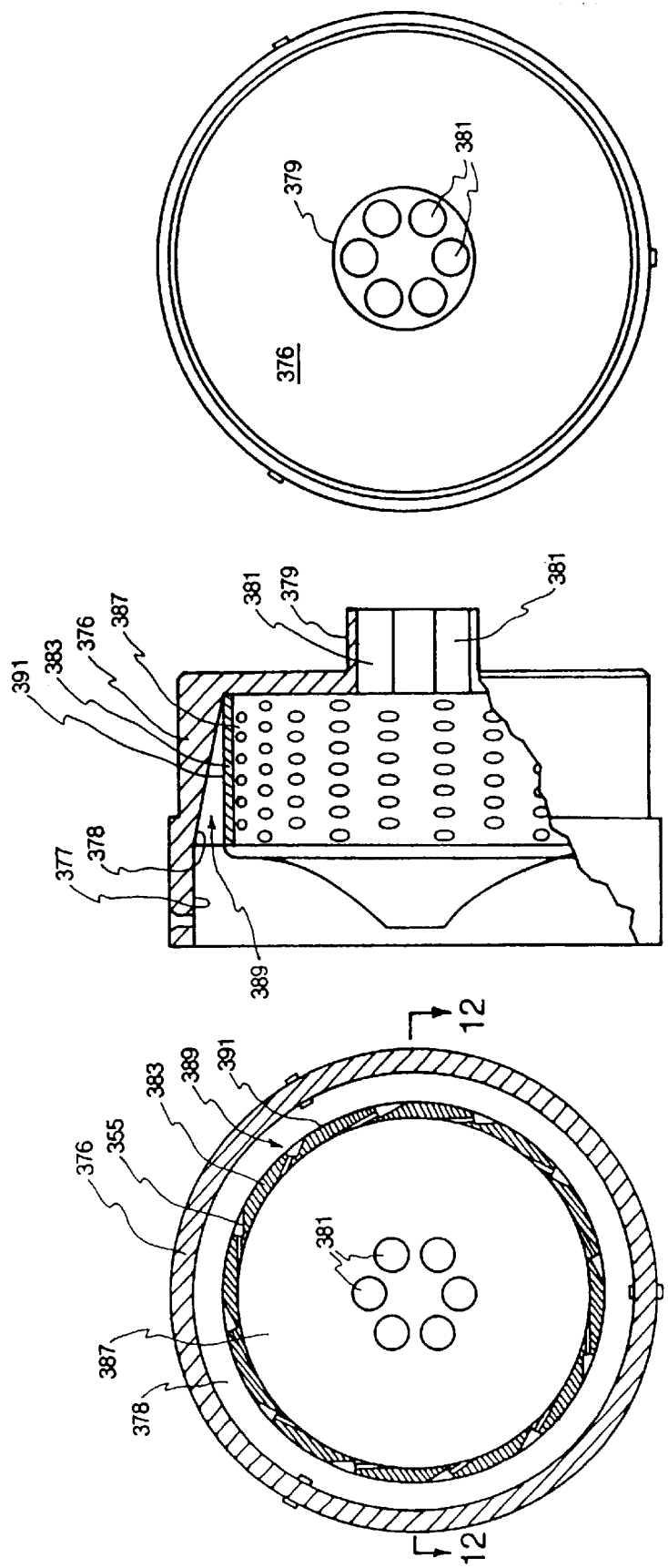

FIGS. 11–13 illustrate an alternate embodiment of a jacket-chamber assembly for use in a plurality of vortex chamber configurations such as that illustrated in FIG. 7. Specifically, a jacket 376 is illustrated as having a constant diameter inside surface 377, a variable diameter inside surface 378, an output port 379, and output apertures 381. The chamber housing 383 is shown as having a plurality of apertures 385 formed at an angle therein and leading tangentially into a vortex chamber 387. A variably spaced gap 389 is formed between the interior surface 378 of housing 376 and the exterior surface 391 of the vortex chamber 383.

FIG. 14 shows another alternative embodiment of a vortex chamber according to the present invention. A chamber housing 380 having an exterior surface 382 and an inner chamber wall 384 defines a vortex chamber 386. To increase the turbulence of a vortical flow within the chamber 386, and to break down into smaller particles any non-vaporized particles in the vortical flow, steps 388 are formed on the inner chamber wall 384. As shown, each step 388 comprises a ramp surface 390 and a transverse surface 392. A plurality of apertures ramp 394 are formed in the housing 380 and intersect the inner chamber wall 384 at transverse surfaces 392. As a fluid flows through the vortex chamber 386, the steps 388 cause relatively small eddies to be created adjacent to the various transverse surfaces 392 which enhances the turbulence of the flow through the chamber 386.

As an alternative or additional manner of increasing the turbulence of a vortical flow within the chamber 386, and to break down into smaller particles any non-vaporized particles in the vortical flow as well as enhance the vaporization of the non-vaporized particles, the inner chamber wall 384 may comprise a textured surface. The textured or irregular surface may be formed by heavy grit sand blasting or applying a type of glass beading. A textured or irregular inner chamber wall surface will tend to cause fluid to flow through the chamber 386 in a more turbulent manner. When non-vaporized particles collide with the textured inner chamber wall surface, the non-vaporized particles will spread apart, break down into smaller particles, and vaporize more readily as compared to a smooth inner wall surface.

FIG. 15 illustrates still another alternative embodiment of a vortex chamber assembly according to the present invention. A chamber housing 570 comprises an exterior surface 572 and interior surfaces 574, 576, 578, 580, and 582. The interior surfaces 574–582 are each substantially cylindrical and define, respectively, vortex chambers 584, 586, 588, 590, and 592.

Apertures 594 are formed tangentially, in an array with offset columns and rows, in the chamber housing 570 to allow the input of fluid tangentially into each vortex chamber 584–592. This tangential input of fluid creates a turbulent vortical flow of fluid through the vortex chambers which breaks down the fluid into smaller particles and vaporizes remaining liquid particles in the vortical flow. The apertures 594, as shown, are arranged in a plurality of rows and in a plurality of columns, preferably staggered relative to one another, to further enhance the turbulent nature of the flow through the chambers 584–592.

A cylindrical output flange 596 comprises an exterior surface 598 and an interior surface 600. The output flange is attached to an upstream end 602 of the chamber housing 570. The interior surface 600 defines the output from vortex chamber 584 of the vortex chamber housing 570. As illustrated, the vortex chambers 584–592 have sequentially decreasing diameters. That is, the diameter of the inside surface 582 is smaller than the diameter of inside surface 580, which is, in turn, smaller than the inside surface of surface 576, which is smaller than the inside surface 574. Given this configuration, as the fluid passes through the chambers 584–592 in a vortical flow having a low pressure end at the output 604 and a high pressure end adjacent to an upstream end 606, the tendency for the chambers closest to the low pressure end (chambers 584 and 586) to receive more flow through the apertures 594 than the chambers closest to the high pressure end 604 (chambers 590 and 592) is significantly reduced.

Additionally, to enhance the vaporization of a fluid as it passes through the chambers 584–592, appropriately sized nozzles 608 (FIG. 15) are positioned at an upstream end of each of the chambers 584, 586, 588, and 590, respectively. The nozzles 608 cause the fluid passing through the vortex chambers to be subjected to additional pressure differentials, thus enhancing the vaporization and break down of fluid particles. The nozzles 608 are preferably sized so as to be secured within the upstream end of the chambers 584–590 by a press-fit attachment.

FIG. 16 discloses a yet additional embodiment of the present invention. As shown, FIG. 16 discloses a vortex configuration 611 comprising a chamber housing 612 having an exterior surface 614 and interior surfaces 616, 618, 620, 622, and 624. The internal surfaces 616–624 are substantially cylindrical and respectively define vortex chambers 626, 628, 630, 632, and 634. Apertures 636 are formed tangentially relative to interior surfaces 616–624 of the vortex chambers 626–634. The apertures 636 are formed in an array in the chamber housing 612 to allow the input of fluid tangentially into the vortex chambers 626–634. This tangential input of fluid creates a vortical flow through the vortex chamber for breaking down into smaller particles and further vaporizing or homogenizing liquid particles in the vortical flow.

A cylindrical output flange 640 is attached to an end 642 of the chamber housing 612. The output flange 640 comprises an interior surface 644 and an exterior surface 646. An output port 648 is defined by the output flange interior surface 644. The output flange 640 is similar to the output flange 596 (FIG. 17) except that the diameter of the inside surface 644 is smaller than that of the inside diameter 600 (FIG. 17). Additionally, the output flange 640 includes an aperture 650, through which a screw (not shown) can be selectively inserted as a way to adjust the flow resistance through the output member 640. The more the screw is advanced into the output port 648, the more air resistance is imparted to the vortical flow as the vortical flow passes through the output port 648.

In general, the air resistance through a vortex configuration can be varied by changing the diameter of the output aperture and/or changing the diameter of the passageways between adjacent vortex chambers within the vortex configuration. The embodiment of FIG. 15 shows a relatively large output and relatively small passageways between adjacent vortex chambers due to the nozzles 608. Conversely, the embodiment of FIG. 16 shows a smaller output and larger passageways between chambers. In some applications it has been found that the embodiment illustrated in FIG. 16 is preferable to the embodiment of FIG. 15.

FIG. 17 shows yet another alternate embodiment of a vortex chamber housing according to the present invention. This embodiment shows a vortex chamber housing 940 generally comprising a bottom wall 942 and a perpendicularly extending cylindrical wall 944. The cylindrical wall 944 comprises an inside surface 946, a top edge 947, and an outside surface 948. A vortex chamber 952 is defined by the inside surface 946 and the bottom wall 942. The vortex chamber housing 940 may be used in a manner similar to that of the vortex chamber housing 54 illustrated in FIG. 1 and described above.

A series of elongated tangential slots 950 are formed through the wall 944 from the outside surface 948 to the inside surface 946 for delivering a fluid tangentially into the vortex chamber 952 relative to the vortical flow of fluid inside the chamber. Each slot 950 is shown as extending without interruption from the top edge 947 of the wall 944 to the chamber housing bottom wall 942. The slots 950 are oriented tangentially to the inside cylindrical surface 946 of the annular wall 944 to permit fluid to be introduced tangentially to the vortical flow into the vortex chamber 952 of the vortex chamber housing 940.

Introducing fluid tangentially into the chamber 952 through the elongated slots 950 creates a continuous sheet of moving fluid passing rapidly across the vortex chamber interior surface 946 adjacent the respective slots 950. This substantially prevents any non-vaporized particles within the flow of fluid from congregating on the interior surface 946. As droplets of non-vaporized fluid particles approach or contact the inside surface 946, such nonvaporized particles are blown away from the inside surface by new fluid-flow particles entering the vortex chamber 952 through the slots 950. Any number of slots 950 may be employed to achieve the desired results. Additionally, different widths of the slots 950 may be used. The slots 950 may be formed in the annular wall 944 with a laser, a circular saw, or by any other suitable method. As one example, slots 950 may have a width of approximately 0.01 inches.

FIGS. 18 and 19 illustrate another alternate embodiment of a venturi according to the present invention. This embodiment shows a venturi 954 comprising a housing 956 and a series of tangential apertures 958 formed in the housing 956. The tangential apertures extend from a housing exterior surface 955 to a housing interior surface 957. The apertures 958 are formed tangentially in the housing 956 to permit fluid, such as an air/fuel mixture, to be inserted into the venturi interior 960 tangentially through the apertures 958 to enhance the turbulence of the flow through the venturi 954.

As shown, the tangential apertures 958 are formed within a narrow throat portion 959 of the venturi 954. In the narrow throat portion 959, the speed of the fluid F passing through the venturi 954 is at a maximum. By introducing a second fluid tangentially into the venturi interior 960 through the tangential apertures 958 in the narrow throat portion 959, the turbulence and mixing of the two fluids is enhanced. Delivery of the second fluid tangentially into the venturi interior 960 through the tangential apertures 958 causes the flow through the venturi interior 960 to spin, thus increasing the turbulence of the flow. The enhanced turbulence of the flow through the venturi 954 further enhances the vaporization and homogenization of the fluid passing through the venturi 954. Accordingly, as the fluid flow F passes through the venturi from the venturi entrance 962 to the venturi 964, the flow is intersected by a tangential flow of a second fluid, such as an air/fuel mixture, entering the venturi interior 960 through the tangential apertures 958 to create a turbulent, and substantially helical, flow through the venturi 954.

Figure 20:
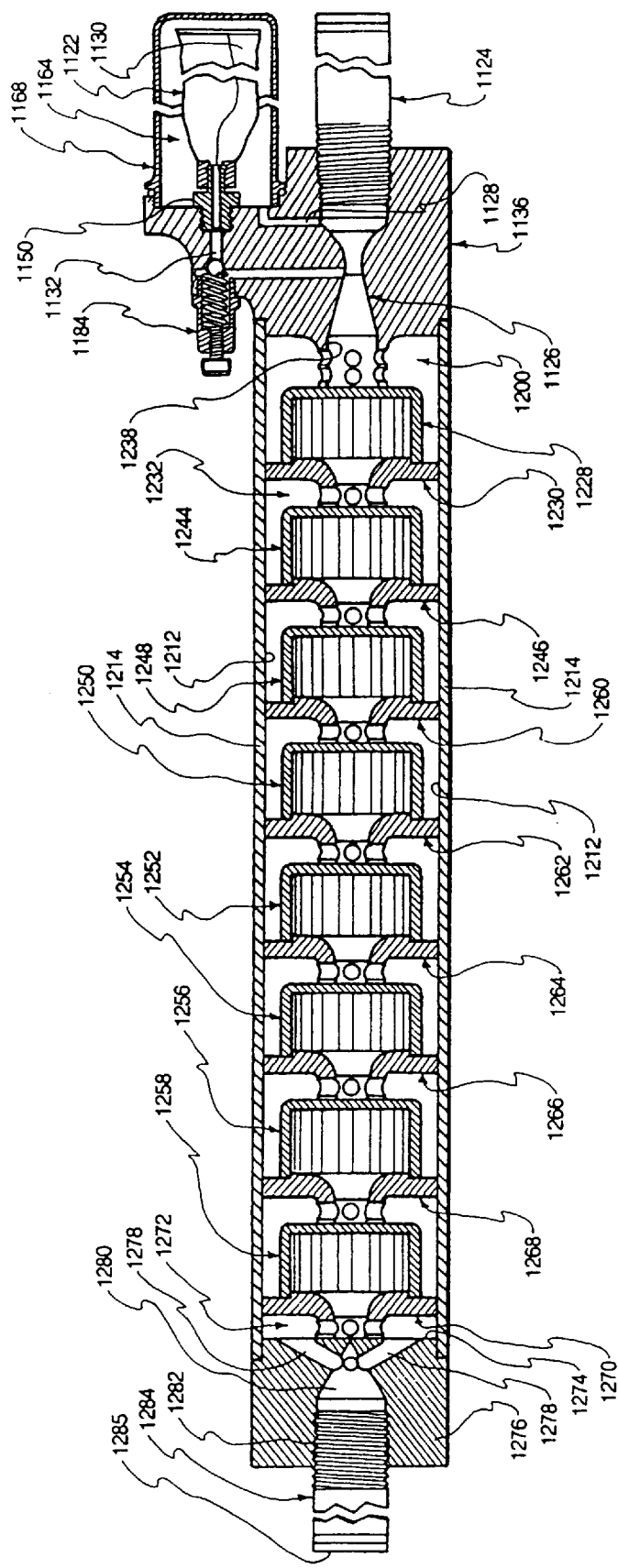
Figure 21:
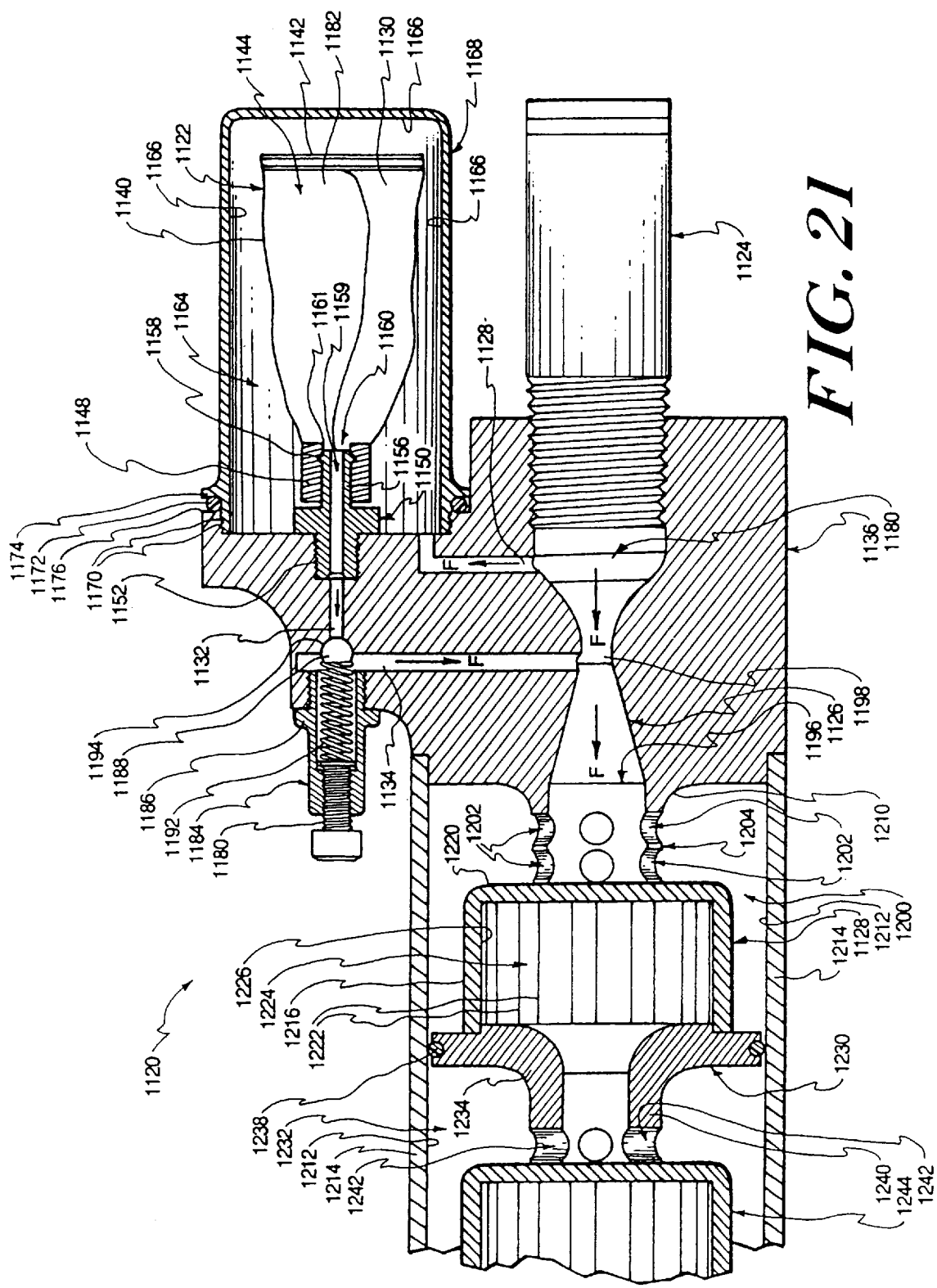
Figure 22:
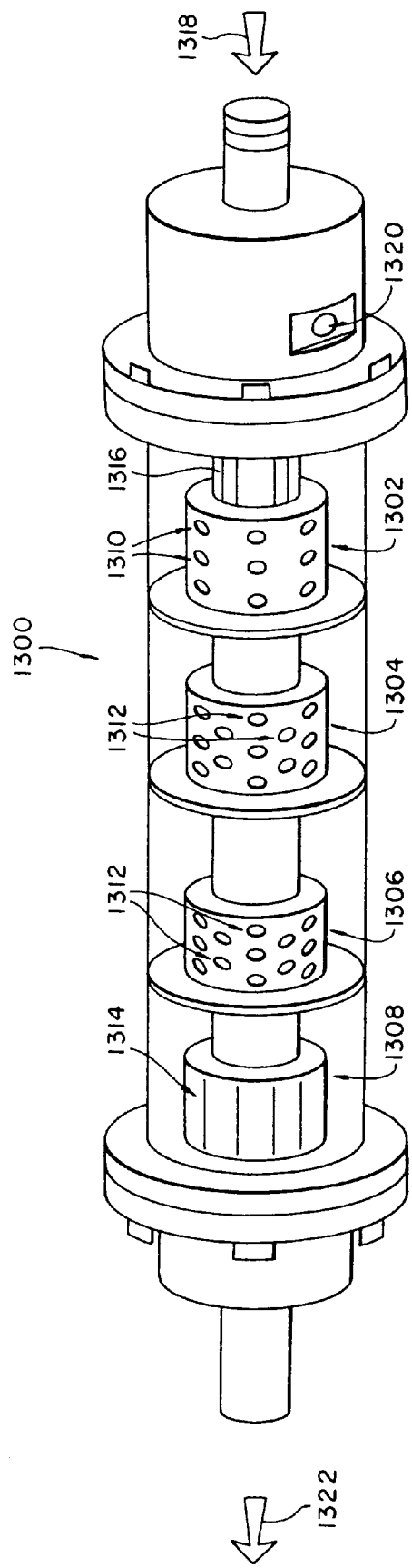

FIGS. 20 and 21 illustrate a yet additional alternative embodiment of the present invention, specifically in relation to uses in the field of inhaler-type medications. This embodiment shows a fluid vaporization system 1120 generally comprising a compressible container 1122, a supply of pressurized gas 1124, a venturi 1126, a plurality of vortex chamber housings 1128, 1244, 1248, 1250, 1252, 1254, 1256, 1258, and a system output 1128. Generally, by introducing pressurized gas into the system 1120, a fluid flow 1130 is forced out of the compressible container 1122 and is caused to flow through conduits 1132 and 1134 (formed in the base 1136) and into the venturi 1126 (also formed in the base 1136). In the venturi 1126, the fluid 1130 is mixed with pressurized gas and is discharged from the venturi 1136 as an aerosol through the venturi outlet opening 1138. The fluid then passes through a series of vortex chamber housings for breaking down into smaller particles and further vaporizing any non-vaporized or partially vaporized particles in the flow. Lastly, the fluid is output from the system through the system output 1128.

Specifically, as shown in FIG. 21, the compressible container 1122 is illustrated as comprising a bag having a flexible side wall 1140 and a flexible base 1142. The flexible wall 1140 and flexible base 1142 define a hollow interior 1144 within the compressible container 1122. As the compressible container 1122 is compressed, the volume of the hollow interior of 1144 is reduced, thus increasing the pressure within the hollow interior 1144.

A compressible fluid container output port 1160 is defined by an interior surface 1161 of a connector 1148. Advantageously, the connector 1148 is formed of a pliable material, such as rubber. The connector 1148 is coupled with the base 1136 via a barbed connector 1150. The barbed connector 1150 is shown as comprising a threaded portion 1152, a shoulder 1154, and a barbed extension 1156. A raised barb 1158 is formed on the extension 1156 to allow a resistance or interference fit between the barbed connector 1150 and the connector 1148 of the container. The barbed connector 1150 further comprises a passageway 1159 extending from the output port 1160 to the conduit 1132 to permit the fluid 1130 within the hollow interior 1144 of the compressible container 1122 to pass from the container 1122 into the conduit 1132. Accordingly, in the assembled configuration shown in FIGS. 20 and 21, the threaded portion 1152 of the connector 1150 is threadedly engaged with the base 1136.

The compressible container 1122 is, in turn, removably secured by a resistance or an interference fit with the barbed connector 1150 by pressing the pliable connector 1148 over the extension 1156 so that a tight resistance or interference fit is created between the barbed extension 1156 and the interior surface 1161 of the connector 1148.

The compressible container 1122 is shown as being positioned within a pressure chamber 1164 defined by an interior surface 1166 of a pressure housing 1168. The pressure housing 1168 is secured to the base 1136 by threads 1170 formed on one end of the pressure housing 1168 for threadedly engaging the pressure housing 1168 with the base 1136. To create a substantially airtight seal between the base 1136 and the housing 1168, a gasket, such as an O-ring 1172, is positioned, and preferably compressed, between a flange 1174 of the housing 1168 and a contact surface 1176 of the base 1136.

The pressure chamber 1164 is pressurized by receiving pressurized gas from the source of pressurized gas 1124 through a pressurized gas conduit 1178. The source of pressurized gas may advantageously be coupled with any of a variety of suitable devices, such as a pump or tank of pressurized gas. Further, the pressurized gas may comprise air, oxygen, nitrous oxide or any other suitable gas.

The pressurized gas conduit 1178 is shown as being formed in the base 1136 and as extending from venturi inlet opening 1180 to the pressure chamber 1164. By passing pressurized gas through the conduit 1178 into the pressure chamber 1164, the pressure within the pressure chamber 1164 increases. This increase of chamber pressure causes the compressible container 1122 to compress, thus squeezing the fluid 1130 out of the container 1122 through the output port 1160 and the connector passageway 1159.

As shown in FIG. 21, the contents of the compressible container 1122 may comprise liquefied fluid 1130 and, in some instances, an amount of gas-phase fluid, such as air 1182. The system 1120 may be used to vaporize a wide range of fluids. In one embodiment, the liquefied fluid 1130 to be vaporized comprises a medicinal preparation to be administered to a patient by inhalation. Preferably, as the fluid exits the system through the system output 1128, only a small percentage of the non-vaporized fluid particles are greater than five microns in size. By vaporizing a fluid medicinal preparation by passing it through the system 1120, the medicinal preparation may be effectively administered to a patient by inhalation.

A flow regulator or ball valve assembly 1184 is coupled to the fluid conduit 1132 extending from the output port 1160. The flow regulator 1184 is shown as generally comprising a regulator housing 1186, a ball 1188 which seats into an appropriately sized cavity, an adjustment screw 1190, and a bias member 1192. The flow regulator housing 1186 is removably secured to the base 1136 by a threaded engagement. As shown, the ball 1188 seats within a spherical opening 1194 formed in the base 1136. The ball 1188 is biased against the spherical opening 1194 by means of a bias member 1192. As illustrated in FIG. 21, the bias member 1192 may comprise a conventional coil spring. In this configuration, as the pressure within the hollow interior 1144 of the compressible container 1122 increases, the pressure within the conduit 1132 increases correspondingly, thus overcoming the bias and pushing the ball 1188 away from the spherical opening 1194 to permit fluid to pass by the ball 1188 from the conduit 1132 into the conduit 1134.

The amount of pressure necessary to unseat the ball 1188 from the spherical opening 1194 may be adjusted by adjusting the compression of the bias member 1192. The compression, and thus the force exerted by the bias member 1192, is readily adjusted by advancing or withdrawing the adjustment screw 1190 relative to the housing 1186. The farther the screw 1190 is advanced into the housing 1186, the more compressed the bias member 1192 will be and, consequently, the more pressure will be required to unseat the ball 1188 to permit fluid to pass by the regulator assembly 1184. Conversely, as the screw 1190 is withdrawn from the housing 1186, the compression of the bias member 1192 is decreased, and thus a lesser pressure within the conduit 1132 will be required to unseat the sphere 1188.

The ball valve assembly 1184 is only one of many different regulators that can be effectively used to control the flow of fluid between the conduits 1132 and 1134. It is to be understood that any suitable valve or other flow-regulating devices may be effectively employed.

In addition to supplying pressurized gas to the pressurized gas conduit 1178, the source of pressurized gas 1124 also feeds pressurized gas into the venturi 1126 through a venturi inlet opening 1180. The venturi 1126 generally comprises the venturi inlet opening 1180, a venturi outlet opening 1196, and a narrow throat portion 1198. The narrow throat portion 1198 is shown as being positioned between the venturi inlet opening 1180 and the venturi outlet opening 1196.

As a flow F of pressurized gas from the pressurized gas source 1124 passes through the venturi 1126, the narrow throat portion 1198 causes the velocity of the pressurized gas to substantially increase. The high speed of the gas through the venturi throat portion 1198 creates a low pressure region at the venturi throat portion 1198. As shown, the narrow throat portion 1198 is in fluid communication with the conduit 1134. The low pressure region at the narrow throat portion 1198 helps to draw fluid from the conduit 1134 into the high-speed, low-pressure gas flow through the venturi throat portion 1198. As the fluid 1130 passes through the conduit 1134 into the narrow throat portion 1198, the fluid 1130 is mixed with the pressurized gas from the pressurized gas source 1124. Because of the high velocity of the gas passing through the narrow throat portion 1198 and the pressure differentials created by the venturi 1126, the fluid 1130 advantageously exits the venturi 1126 through the venturi outlet opening 1196 as an aerosol.

After exiting the venturi 1126, the fluid is discharged into a mixing chamber 1200 through a plurality of apertures 1202 formed in a hollow boss 1204. As shown in FIG. 21, the boss 1204 is formed as one piece with the base 1136 and comprises a hollow interior 1206 in fluid communication with the venturi outlet opening 1196. Thus, upon exiting the venturi 1126 through the venturi outlet opening 1196, the fluid passes into the mixing chamber 1200 through the apertures 1202 formed in the boss 1204.

The mixing chamber 1200 is defined by a base exterior surface 1210, an inside surface 1212 of a tube 1214, and the exterior surface 1216 of the venturi chamber housing 1128. The vortex chamber housing 1128 is configured and functions in the same manner as the vortex chamber housing 940 described above and illustrated in FIG. 17.

As shown in FIG. 21, the vortex chamber housing 1128 further comprises an exterior bottom surface 1220 which is positioned adjacent to and abuts the boss 1204, causing the fluid passing through the boss hollow interior 1206 to exit the hollow interior through the apertures 1202. After the flow F of fluid enters the mixing chamber 1200, the fluid next passes into the vortex chamber 1124 through tangential apertures 1220 formed in the vortex chamber housing 1128. The tangential slots 1222 are identical to the elongated tangential slots 950 described above and illustrated in FIG. 17. The tangential slots 1222 permit the fluid to be directed tangentially into the vortex chamber 1224. Due to the tangential orientation of the slots 1222, the fluid is directed tangentially into the vortex chamber 1224 to create a vortical flow of fluid within the vortex chamber 1224.

An output fixture 1230 is attached to the vortex chamber housing 1128 for directing the fluid from the vortex chamber 1224 into a mixing chamber 1232. The output fixture 1230 is illustrated as being attached to the vortex chamber housing 1128 by a press-fit attachment, but could also be secured to the vortex housing by a number of conventional methods.

The output fixture 1230 is shown in FIG. 21 as comprising a body 1234 having an annular groove 1236 formed about the periphery of the body 1234. A gasket, such as O-ring 1238, may be positioned within the groove 1236 to prevent the fluid from passing directly from the mixing chamber 1200 to the mixing chamber 1232 without passing through the vortex chamber 1224. The output fixture 1230 further comprises a hollow interior 1240 and apertures 1242 for directing the fluid from the vortex chamber 1224 through the output fixture 1230 into the mixing chamber 1232.

Upon exiting the output fixture 1230 through the apertures 1242, the fluid passes through the mixing chamber 1132 and through the vortex chamber housing 1244 in the same manner as the fluid passes through the vortex chamber housing 1128. Likewise, the fluid exits the vortex chamber housing 1244 through an output fixture 1246 which is configured identical to the output fixture 1230 discussed above and illustrated in FIG. 21. In this same manner, as shown in FIG. 20, the fluid passes through the vortex chambers 1248, 1250, 1252, 1254, 1256, and 1258 as well as through output fixtures 1260, 1262, 1264, 1266, 1268, and 1270. As shown, the vortex chamber housings 1244, 1248, 1250, 1252, 1254, 1256, and 1258 are each configured and function in a manner identical to that of the vortex chamber housing 1128. Likewise, the output fixtures 1246, 1260, 1262, 1264, 1266, 1268, and 1270 are configured and function in a manner identical to that of the output fixture 1230 described above and illustrated in FIG. 21. Accordingly, no further description of these features is necessary.

Upon exiting the output fixture 1270 (FIG. 20), the fluid enters a discharge chamber 1272 defined by the output fixture 1270 and an inside surface 1274 of an output housing 1276. As shown, the output housing 1276 is rigidly secured to the tube 1214. The inside surface of the output housing 1276 while the discharge housing 1276 is illustrated as being attached to the tube 1214 by a press-fit attachment, the discharge housing 1276 could also be affixed to the tube 1214 by a variety of methods, including adhesion or a threaded engagement The discharge housing 1276 further comprises a plurality of output channels 1278 for passing the fluid from the discharge chamber 1272 into a discharge orifice 1280. The discharge orifice 1280 further comprises a threaded portion 1282 to permit a conventional threaded connector such as a hose nipple 1284 to be threaded into the discharge housing 1276 for receiving fluid from the discharge aperture 1280. An output end 1285 of the conventional connector 1284 may conveniently be coupled to a variety of fluid receiving devices, such as inhalation mouthpieces, or other structures for receiving a substantially vaporized flow of the fluid 1130.

The operation of the embodiment illustrated in FIGS. 1–6 is described below. Liquid, such as fuel, is electronically controlled, metered, and sprayed as an aerosol through the output ports 46 of the fuel injectors 38 into the preliminary mixing chamber 44. While fuel is the fluid referred to herein, other fluids, such as medicine and waste liquid may also be vaporized and homogenized using the devices and methods disclosed.

As fuel is sprayed into the preliminary mixing chamber 44, the throttle plate 84 opens to permit an amount of air to be input into the venturi 82. The amount of air permitted to pass by the throttle plate 84 is proportional to the amount of fluid sprayed into the preliminary mixing chamber by the output ports 46 of the fuel injectors 38. An engine-created vacuum pulls the fluid from the mixing chamber 44 through the apertures 66 formed in the chamber housing 54.

When the engine operates, a partial vacuum is produced in the engine intake manifold (not shown). With the throttle plate in a closed position, the lower pressure air/fuel mixture in the preliminary mixing chamber 44 is drawn tangentially through the apertures 66 into the vortex chamber 64. Specifically, air for the vortex chamber is introduced through the slot 94 and passes through the ambient air channel 100 and the conduit 102 into the ambient air conduit 50. From the ambient air conduit 50, ambient air is introduced into the preliminary mixing chamber where the ambient air mixes with the aerosol fuel prior to entering the apertures 66 as an air/fuel mixture.

The air/fuel mixture is introduced substantially tangentially into the vortex chamber 64 where the fluid is rotationally accelerated due to incoming fluid through the apertures 66. The amount of fluid entering the various apertures 66 is substantially equalized by the presence of the jacket 60. The inside surface 56 of the jacket restricts the flow of fluid entering the apertures according to the location of the aperture relative to the output port 70, which comprises a low pressure end of the flow passing through the vortex chamber 64. Essentially, the jacket provides a heightened restriction on apertures closer to the output port 70 and a lesser, if any, restriction of the apertures farthest from the low pressure end (output port 70).

Once the fluid is inserted into the vortex chamber 64, the fluid is rotationally accelerated, which causes any non-vaporized particles of fluid within the flow to break down into smaller particles, to be vaporized, or both. When the fluid reaches the output port 70, the fluid passes from the chamber 64 into the intermediate chamber 136 as a spinning column of fluid. In the intermediate chamber 136, the fluid is enfolded upon itself, thus breaking up the spinning column of fluid and creating additional turbulence and homogenization of the flow.

The flow is then drawn by the partial vacuum created by the engine manifold through the elongated apertures 106 of the venturi 82. The elongated apertures 106 are significantly larger and more numerous than conventional small circular venturi chamber apertures as they are designed to reduce any pressure drop and to enable a flow of up to 60 CFM. In the venturi 82, the ambient air, admitted by the throttle plate 84, is mixed with the air/fuel mixture as the air/fuel mixture enters through the apertures 106. The ambient air/fuel mixture is further mixed, and at least partially homogenized, within the venturi 82.

The partial vacuum of the engine manifold next draws the fluid through the centrifuge intake opening 144 as the fluid enters the entry chamber 146. The entry chamber serves to further mix and homogenize the fluid and to direct the fluid into the centrifuge chamber 152 tangentially. Specifically, the baffles 150 formed within the entry chamber 146 create a series of tangential passageways 200, 202, and 204 through which the fluid is tangentially drawn into the centrifuge chamber 152 by the partial engine manifold vacuum.

In the centrifuge chamber 152, the fluid is rotationally accelerated which causes the largest or heaviest particles to be moved, due to their mass, toward the perimeter of the centrifuge chamber 152 where these heavier, or more massive, particles collide with the interior surface 156 and are further broken down and vaporized.

To reduce the volume of the centrifuge chamber 152, it is advantageous that the height of the side wall 156 be smaller than the inside diameter 114 of the venturi 82 at the venturi output 110. Additionally, to reduce the volume of the centrifuge chamber 152 and to enhance the centrifugal flow in the chamber 152, the extension member 162 extends from the centrifuge housing top wall 160.

The fluid is then drawn into the four outputs 154 by the engine vacuum. As the lighter particles of the flow centrifugally advance toward the center of the centrifuge housing 152, they are directed, at an angle, by the conically-shaped portion of the centrifuge contoured top surface 170 into the apertures 182 formed in the conically-shaped portion 180 and into the four outputs 154. By discharging the fluid from the centrifuge chamber in the manner described, a more uniform hydrocarbon distribution is obtained due to the hydrocarbon's generally tendency to be positioned towards the outside of the centrifugal flow in the centrifuge chamber. In contrast, where only one output port is employed, the centrifuge discharge is less uniform due to the tendency of hydrocarbons to be positioned toward the outside of the centrifugal flow.

Turning now to the embodiment of the invention illustrated in FIG. 7, the vortex configuration 220 is supplied with aerosol fuel by fuel injectors 222. The fuel injectors 222 spray fuel into a preliminary mixing chamber 242. Ambient air is also introduced into the preliminary mixing chamber 242 via the ambient air conduit 244. In the preliminary mixing chamber, the aerosol fuel and the ambient air are mixed so as to enter the vortex chamber 248 through the apertures 260 as an air/fuel mixture.

In a manner similar to the jacket 60 (FIG. 1), the jacket 272 serves as a pressure differential supply to normalize the amount of flow through the various apertures 260. The air/fuel mixture enters the vortex chamber 248 through the apertures 216 in a manner similar to that described in connection with the vortex chamber 54 and aperture 66 of FIG. 1. As the air/fuel mixture exists the U-shaped output port 340, the mixture enters into a mixing chamber 350 prior to entering the vortex chamber 250 through apertures 262. In this configuration, the apertures 262 receive the air/fuel mixture exclusively from the output from the vortex chamber 248 to maintain a substantially constant air/fuel ratio as the air/fuel mixture passes through the chambers 248 and 250.

Subsequently, the air/fuel mixture exits the U-shaped output port 242 and enters into mixing chamber 352 prior to entering the vortex chamber 252 through apertures 264. Again, the air/fuel ratio of the air/fuel mixture remains substantially constant as the fluid passes through the vortex chambers 250 and 252.

After exiting the output port 344 of the chamber housing 228, the fluid continues to pass through the mixing chamber 354, apertures 266, and vortex chamber 254 in a manner identical to that described in connection with the vortex chamber 252. Upon exiting the U-shaped output port 346, the fluid enters the mixing chamber 356, passes through the apertures 268 into the final chamber 256 prior to exiting the output port 348.

By passing through the five chambers 248–256, the fluid becomes increasingly vaporized and transformed in a gaseous phase as it advances from one chamber to the next. Accordingly, this embodiment permits an air/fuel mixture to pass through several vortex chambers while maintaining a substantially constant air/fuel ratio.

An alternate embodiment of a vortex chamber housing is illustrated in FIG. 17. In operation, the vortex chamber housing 940 receives fluid through the tangential slots 950 into the chamber interior 952 to create a vortical flow of fluid within the chamber interior 952. The elongated slots 950 introduce the fluid tangentially into the chamber interior as a sheet of fluid along the interior surface 946 of the vortex chamber housing to prevent liquid particles from congregating on the interior surface 946. As the fluid spins vertically within the chamber 952, the pressure differentials and the overall turbulence of the flow within the chamber 952 cause the fluid to be vaporized and homogenized.

FIGS. 18 and 19 illustrate an alternative embodiment of a venturi 956 formed in accordance with the principles of the present invention. In operation, the venturi 956 receives a flow of fluid through the venturi inlet opening 962. This flow of fluid is then mixed with an air/fuel mixture which enters the venturi interior 960 through tangential apertures 958 formed in the wall 956 to create a helical flow of fluid through the venturi 954. Introducing the air/fuel mixture tangentially into the venturi interior 960 causes the flow through the venturi 954 to spin helically. Advantageously, the air/fuel mixture is introduced in the narrow throat portion 959 of the venturi interior 960 because the narrow throat portion 959 comprises the region of fastest air flow within the venturi 954. By creating a helical flow of fluid through the venturi 956, the turbulence, and thus the vaporization and homogenization, of the fluid is substantially enhanced.

As discussed above, FIGS. 20 and 21 illustrate a yet additional embodiment of the invention. In this embodiment, positive pressure is provided into the system 1120 through a positive pressure source 1124 which delivers gas, under pressure, into the venturi inlet opening 1180 and into the pressurized gas conduit 1178. The pressurized gas passes through the pressurized gas conduit 1178 into the pressure chamber 1164. As the pressure within the pressure chamber 1164 increases due to the pressurized gas, the compressible container 1122 is compressed, thus reducing the volume and increasing the pressure of the container of hollow interior 1144. As the compressible container 1122 is compressed, the fluid 1130 within the container 1122 is forced out of the container 1122 through the output port 1160, through the passageway 1159, and into the fluid conduit 1132.

The flow of fluid from the fluid conduit 1132 to the conduit 1134 is controlled by the regulator 1184. In the biased position illustrated in FIG. 21, the sphere 1188 is biased against the spherical seat 1194 to prevent fluid from flowing from the conduit 1132 to the conduit 1134. As the pressure within the conduit 1132 increases, however, the bias against the spherical seat 1194 is overcome and the sphere 1188 is dislodged from the spherical seat 1194 to permit the fluid to pass from the conduit 1132 to the conduit 1134.

The bias of the sphere 1188 against the spherical seat 1194 can be adjusted by advancing or withdrawing the screw 1190 within the housing 1186. As the screw 1190 is advanced into the housing 1186, the spring 1192 is compressed, thus increasing the bias on the sphere 1188. Conversely, as the screw 1190 is withdrawn from within the housing 1186, the spring 1192 is decompressed, thus reducing the amount of bias on the sphere 1188. With a reduced bias on the sphere 1188, a lesser pressure in the conduit 1132 is required to unseat the sphere 1188 and to enable flow from the conduit 1132 to the conduit 1134.

After passing by the regulator 1184, the fluid passes through the conduit 1134 and enters the venturi throat portion 1198 as an aerosol. As the pressurized gas passes through the venturi 1126, the velocity of the gas increases as it passes through the narrow throat portion 1198, thus creating a low pressure region at the narrow throat portion 1198. The low pressure associated with the high velocity flow through the venturi narrow throat portion 1198 helps to draw the fluid through the conduit 1134 into the narrow throat portion 1198.

In the venturi throat portion 1198, pressurized gas from the source of pressurized gas 1124 is mixed with the fluid 1130. After mixing with the pressurized gas, the fluid exits the venturi 1126 through the venturi outlet opening 1196 as an aerosol. From the venturi outlet opening 1196, the fluid passes through apertures 1202 formed in the boss extension 1204 and into the mixing chamber 1200. From the mixing chamber 1200, fluid enters the vortex chamber 1224 through the tangential slots 1222 to create a vortical flow within the vortex chamber 1224 for breaking down into smaller particles and vaporizing any non-vaporized particles in the vortical flow.

The fluid then passes from the vortex chamber 1224 into the mixing chamber 1232 through the apertures 1242 formed in the output fixture 1230. The fluid continues to pass through the subsequent vortex chamber housings 1244, 1248, 1250, 1254, 1256, and 1258 as well as through subsequent output fixtures 1246, 1260, 1262, 1264, 1266, 1268, and 1270 in the same manner as the fluid passes through the vortex chamber housing 1128 and the output fixture 1230 respectively. The fluid is further homogenized and vaporized through each succeeding vortex chamber housing.

Upon exiting the final output fixture 1270, the fluid passes through a discharge chamber 1272 and into the channels 1270 to supply the output orifice 1280 with a supply of substantially vaporized fluid. To facilitate the delivery of the vaporized fluid to its final destination, the fluid may pass through a conventional hose connector 1284.

Another embodiment of the present invention related to vaporizing and nebulizing liquids for inhalation by a patient is shown in FIG. 22. Conceptually, the embodiment for this system 1300 comprises a plurality of stages, with vortex chambers 1302–1308 having differing characteristics. In this embodiment, in the first stage the vortex chamber 1302 has apertures 1310 in parallel rows and columns. In the second and third stages, the vortex chambers 1304 and 1306 have apertures 1312 that are staggered, similar to the apertures 66 of the vortex chamber 64 as shown in FIG. 3. In the final stage, the vortex chamber 1308 has slots 1314, similar to the tangential slots 950 as shown in FIG. 17.

For this embodiment 1300 FIG. 22, the vortex chambers 1304 and 1306 for the second and third stages have smaller apertures 1312 than the apertures 1310 of the first stage vortex chamber 1302. However, the total surface area of the apertures 1312 for each of the second and third stages is the same as the total surface area of the apertures 1310 of the first stage. This is due to the vortex chambers 1304 and 1306 of the second and third stages having more apertures. In other words, although the apertures 1312 are smaller, there are more apertures 1312.

In this embodiment, positive pressure 1318 is provided into the system 1300 in the form of compressed gas or air, typically at 125 psi. Fluid is drawn in through opening 1320. The fluid includes the medicine to be nebulized/vaporized, and can include an inert carrier such as saline solution. Lateral openings 1316 permit the fluid to reach the outside of the vortex chamber 1302 and then enter through the apertures 1310. This is repeated for each stage (not shown).

Variations are possible with this embodiment, including greater or fewer stages, and different combinations of vortex chambers with different aperture patterns 1310, 1312 and slots 1314. Another variation is a configuration in which the first stage creates a large pressure drop, and in the remaining stages each include slight pressure drops, resulting in the final output 1322 being close to atmospheric pressure. This can improve the processing efficiency.

Another variation with all embodiments is to include a heating process. Either the input air 1318 is heated, or the external surface of the system is heated to impart thermal energy to the air and fluid as they move through each stage of the device. For example, for fluid separation purposes such as desalinization, heating the system provides better results, depending on other factors including pressure and the number of vortex chambers. This fluid separation ability is believed to be a kinetic evaporative process, at least in relation the embodiment 1300 of FIG. 22. The present invention can include one or several vortex chambers 1302–1308 which are easily removable to clean and flush off deposited material. Alternatively, the entire system can be soaked, or forward or reverse flushed with fluid to clean out the device.

Another embodiment of the present invention is shown in FIG. 23. This embodiment of the system 1330 comprises a single stage vortex chamber 1340 with a pressure decreasing first section 1341 and a deceleration second section 1343. Compressed air 1318 enters through the intake nozzle 1332. A step down venturi stage 1334 is created by restricting the flow diameter 1336 to approximately 0.250". Next is a step up venturi stage 1338 with a diameter of approximately 0.370". The fluid enters this step up venturi stage 1338 through the fluid intake port 1320, which has a diameter of approximately 0.0625".

The air/fluid mixture then passes out of the first section 1341 and reaches the vortex chamber 1340. For this embodiment, the vortex chamber 1340 includes apertures 1312 arranged in a staggered formation. Specifically, the vortex chamber 1340 has 40 apertures with a hole diameter of approximately 0.035", thereby creating a total surface area of approximately 0.0385 square inches.

The air/fluid exits the vortex chamber 1340 through a step down venturi 1342. This step down venturi 1342 has a venturi opening 1344 with a diameter of approximately 0.0995".

The vortex chamber 1340 is positioned between two annular gaskets 1354 and 1354' which securely hold the vortex chamber in place in the system 1330, and direct the flow of air/fluid through each section. The vortex chamber 1340 and one annular gasket 1354 slide inside the inside wall 1346 of the deceleration second section 1343, as shown by arrow 1350. When in position, they are proximate and are held in place by partitioning wall 1348, the vortex chamber 1340 is positioned inside of deceleration second section 1343.

The deceleration second section 1343 includes a deceleration chamber 1352. When the air/fluid exits the vortex chamber 1340 through the step down venturi 1342, it comes out in a cone shaped swirl. The output 1322 at the end of the deceleration chamber 1352 is the nebulized, atomized or vaporized air/fluid mixture with super fine particles, at approximately atmospheric pressure.

In this embodiment, the complete system 1330 is approximately 5.8" long. The pressure decreasing first section 1341 is approximately 1.275", and the deceleration second section 1343 is approximately 4.6" long. The vortex chamber 1340 and annular gasket 1354, when positioned within the deceleration second section 1343, extend approximately 1.6"

within the deceleration second section 1343. The deceleration chamber 1352 is approximately 3" long. The deceleration second section 1343 has an inside diameter of approximately 1.375".

Test results for this embodiment were conducted with saline solution as the working fluid. Compressed air 1318 at 185 psi (18 cubic feet per minute) was provided through the intake nozzle 1332. A pressure drop to near atmospheric pressure is achieved by the first step down venturi stage 1334 and the second step down venturi 1342. This creates a 185 psi pressure drop as the fluid leaves the vortex chamber 1340 and enters the deceleration chamber 1352. An improvement in the amount of liquid the unit processes is observed, with processing approaching 3 ml per minute. The deceleration chamber 1352 also helps to function as a large particle separator in the case when very fine particles are intermixed with large particles (for example, when nebulizing certain liquids). The deceleration chamber 1352 is very effective in separating these larger particles. When the fluid exits the vortex chamber 1340, it comes out in a cone shaped swirl. The larger particles form a crust just ahead of the venturi opening 1344 (when running Saline). The output at the end of the chamber is just the super fine particles.

Figure 23:
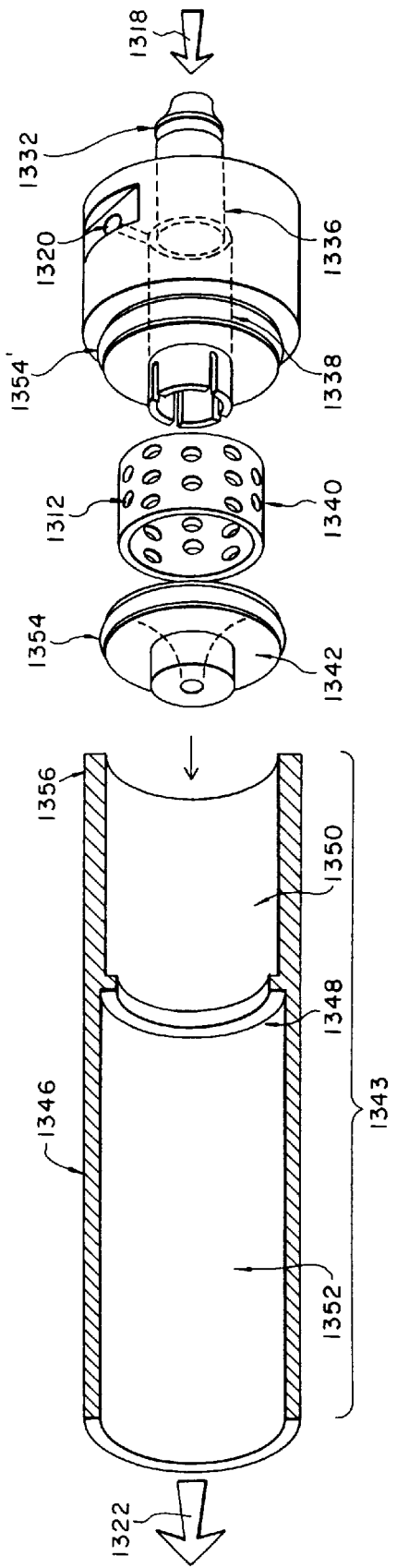
Figure 24:
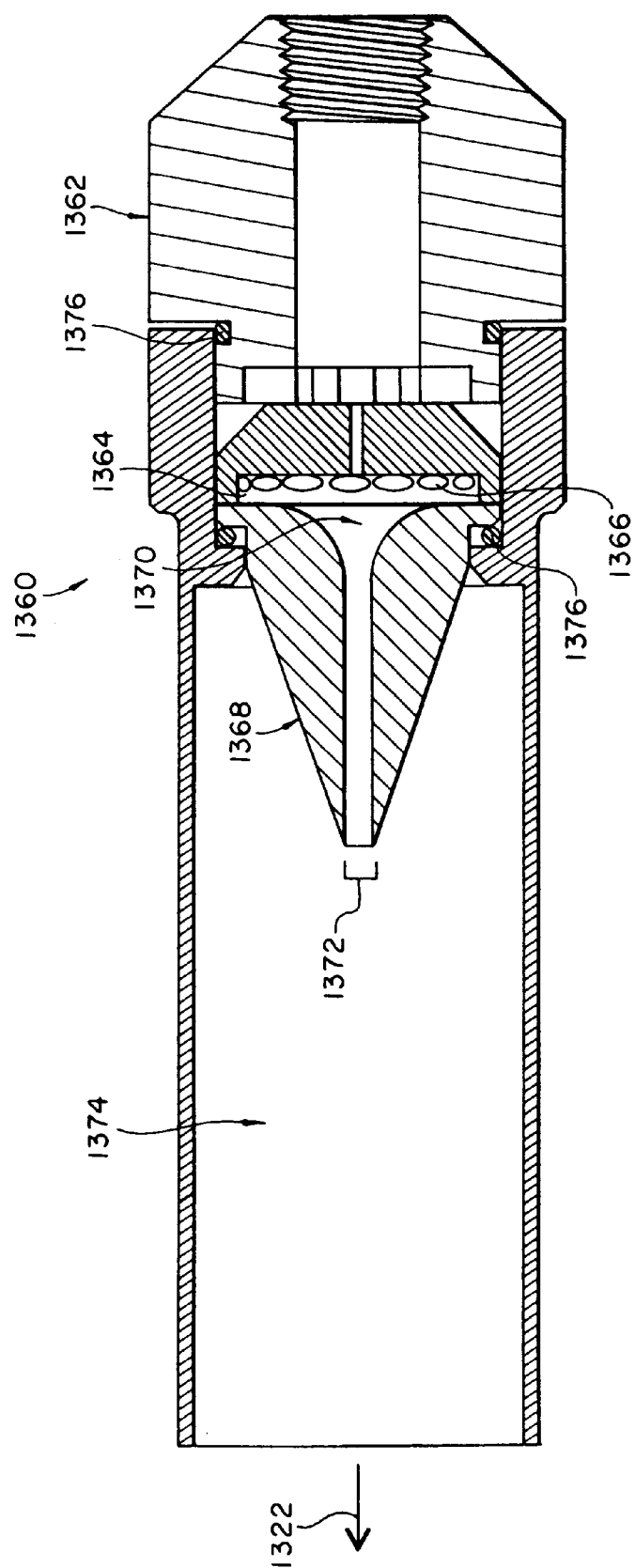

In using the embodiments of FIGS. 23 and 24 for fluid separation, it is believed the process includes a pneumatic/ kinetic evaporative process. The single stage vortex chamber and venturi or nozzle create vortex-related sheer forces on the fluid, to reduce particle size and enhance separation.

Figure 25C:
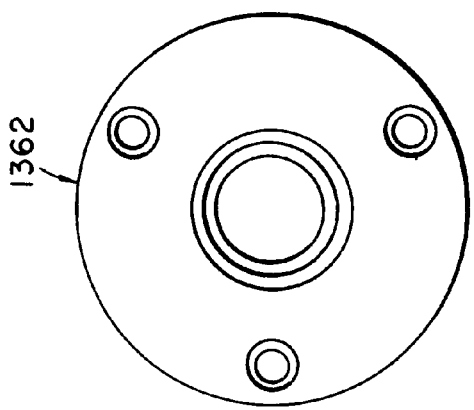
Figure 25B:
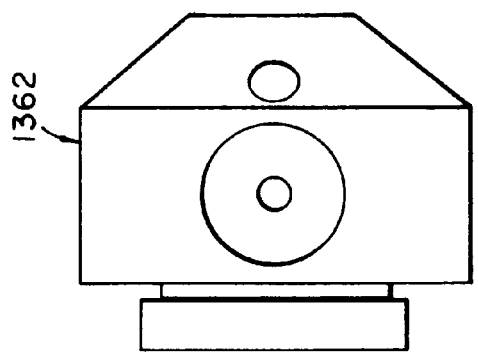
Figure 25A:
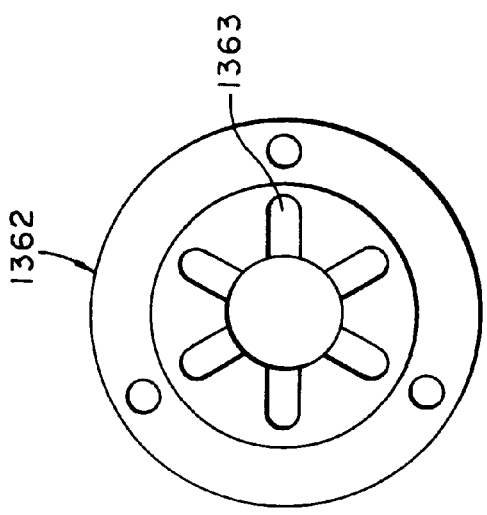
Figure 26C:
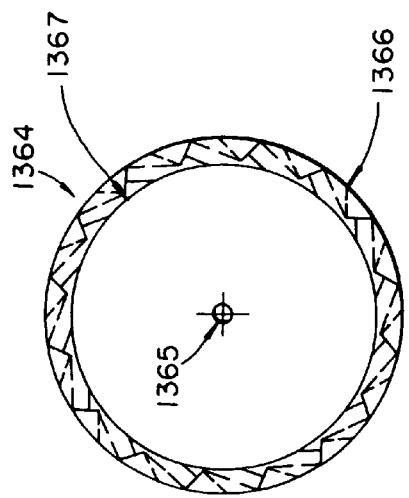
Figure 26B:
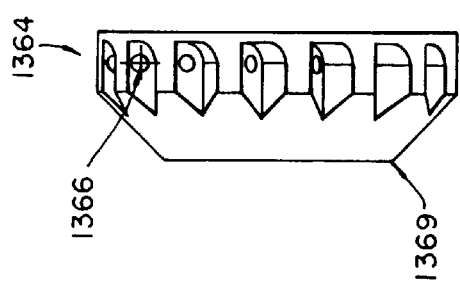
Figure 26A:
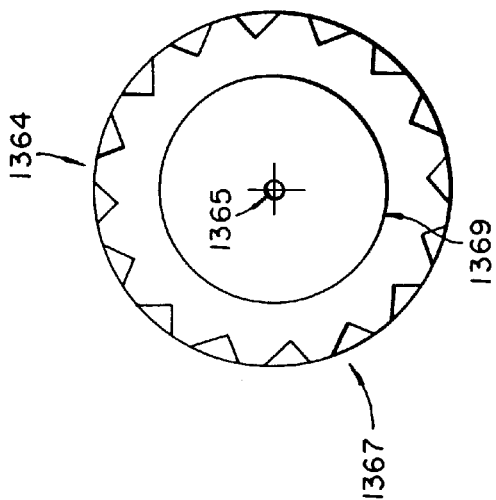

Another embodiment of the present invention related to vaporizing and nebulizing liquids for inhalation by a patient is shown in FIG. 24. This embodiment 1360 is similar to the embodiment 1330 of FIG. 23 in that it includes a single stage vortex processor (chamber) 1364, a step down nozzle 1368 and a deceleration chamber 1374. This embodiment 1360 includes an air-gas input mixer section 1362, which is shown in detail in FIGS. 25A–C. The gas/fluid mixture passes through openings 1363, which have a radius of approximately 0.625". The gas/fluid mixture flows to vortex processor 1364, which is shown in detail in FIGS. 26A–C. The vortex processor 1364 includes a single row of apertures 1366, which pass tangentially through to the central chamber, as shown by 1367. The aperture diameter is approximately 0.055". The inner diameter of the chamber wall of the vortex processor 1364 is approximately 0.084". The vortex processor 1365 has an outside diameter 1361 of approximately 1", an inner diameter 1369 of approximately 0.6250", and a center feed 1335 with a diameter of approximately 0.0460". Of course, all sizes and openings may be varied to enhance preferred performance of the present invention.

As the air/fluid mixture passes through the vortex processor 1364, it enters a venturi chamber 1370 defined by the nozzle 1368. The nozzle 1368 outside tapers to an end, with a constant inner diameter 1372 of approximately 0.0995". The air/fluid mixture emerges into the deceleration chamber 1374 and then emerges out the end of the deceleration chamber 1374 at near atmospheric pressure, as shown by arrow 1322. The sections are connected together using gaskets or O-rings 1376 to provide fluid-proof seals.

Figure 27B:
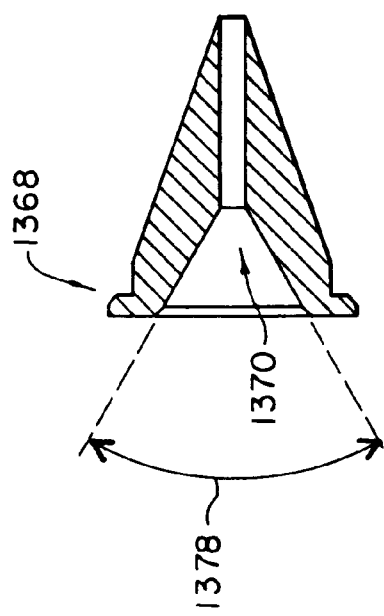
Figure 27A:
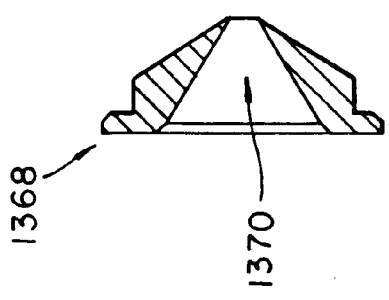

For this embodiment, the deceleration chamber 1374 is approximately 3" long with an interior diameter of approximately 1.1415". The nozzle 1368 extends approximately 1" into the deceleration chamber 1374. The nozzle 1368 defines a venturi chamber 1370 with a tapered inner wall having a radius of approximately 0.25". Variations of the nozzle 1368 is shown in FIG. 27A and B, wherein the nozzle embodiments define a venturi chamber 1370 with walls forming approximately a 60 degree angle (as shown by arrow 1378) reducing the dimension to the opening inner diameter 1372 of approximately 0.0995". The lengths of the nozzle 1368 are varied depending on the desired nebulization, atomization, vaporization or separation performance, for example the short nozzle shown in FIG. 27A or the long nozzle shown in FIG. 27B, with a length of approximately 1".

The systems and methods disclosed are also applicable and useful in the breakdown, vaporization, and homogenization of waste fluids for incineration and waste management. As the waste fluid particles are broken down into extremely small particle sizes, the waste fluid introduced into an incinerator will be burned more efficiently, thereby minimizing pollution and increasing the efficiency of which the waste fluids are incinerated.

Although the invention has been shown and described with respect to illustrative embodiments thereof, various other changes, omissions and additions in the form and detail thereof may be made therein without departing from the spirit and scope of the invention.

What is claimed is:

1. A vortex system for nebulizing a liquid for inhalation, comprising:
    a venturi component, fluidly coupled to a source of compressed gas, and fluidly coupled to a source of said liquid;
    a vortex component, comprising:
        a chamber housing defining a vortex chamber where a vortical flow is generated and the liquid is atomized, the chamber housing being fluidly coupled to said venturi component;
        a plurality of apertures formed in said chamber housing to allow input of fluid tangentially into said vortex chamber to create a vortical flow in said vortex chamber; and
        a chamber output, fluidly coupled to said vortex chamber for discharging fluid from said vortex chamber.

2. The vortex system according to claim 1 wherein said plurality of apertures are arranged in rows and columns in said chamber housing.

3. The vortex system according to claim 2 further including:
    a second vortex component comprising:
        a second chamber housing defining a second vortex chamber, fluidly coupled to said chamber output;
        a plurality of apertures formed in said second chamber housing to allow the input of fluid tangentially into said second vortex chamber to create a vortical flow in said vortex chamber, said plurality of apertures being arranged in rows and staggered columns in said second chamber housing; and
        a second chamber output, fluidly coupled to said second vortex chamber for discharging fluid from said second vortex chamber.

4. The vortex system according to claim 3 further including:
    a third vortex component, identical to said second vortex component, wherein a third chamber housing defining a third vortex chamber is fluidly coupled to said second chamber output.

5. The vortex system according to claim 4 further including:
    a fourth vortex component comprising:
        a fourth chamber housing defining a fourth vortex chamber, fluidly coupled to a chamber output of said third chamber housing;

a series of tangential elongated slots formed in said fourth chamber housing to allow input of fluid tangentially into said fourth vortex chamber to create a vortical flow through the vortex chamber, wherein each tangential slot extends from a top portion to a bottom of said fourth vortex chamber.

6. The vortex system according to claim 1 wherein said chamber housing has an inner chamber wall including a textured surface formed on said inner chamber wall.

7. The vortex system according to claim 1 wherein said chamber housing has an inner chamber wall including a plurality of steps formed on said inner chamber wall.

8. A vortex system for nebulizing a liquid for inhalation, comprising:

a venturi component, fluidly coupled to a source of compressed gas, and fluidly coupled to a source of said liquid;

a plurality of vortex components fluidly coupled in series, each vortex component comprising:

a chamber housing defining a vortex chamber where a vortical flow is generated and the liquid is atomized, the chamber housing being fluidly coupled to a chamber output of a previous vortex component;

a plurality of apertures formed in said chamber housing to allow input of fluid tangentially into said vortex chamber to create a vortical flow in said vortex chamber; and a chamber output, fluidly coupled to said vortex chamber for discharging fluid from said vortex chamber;

wherein a chamber housing of a first one of said plurality of vortex components is fluidly coupled to said venturi component.

9. A vortex system for nebulizing a liquid for inhalation, comprising:

a vortex component, comprising:

a chamber housing defining a vortex chamber where a vortical flow is generated and the liquid is atomized, the chamber housing being fluidly coupled to a source of compressed gas, and fluidly coupled to a source of said liquid;

a plurality of apertures formed in said chamber housing to allow input of fluid tangentially into said vortex chamber to create a vortical flow in said vortex chamber;

a chamber output, fluidly coupled to said vortex chamber for discharging fluid from said vortex chamber; and a deceleration component, fluidly coupled to said chamber output.

10. The vortex system of claim 9, further including:

a venturi component, fluidly coupled to a source of compressed gas, and to a source of said liquid, and fluidly coupled to said chamber housing.

11. The vortex system of claim 9, wherein said chamber output includes a fluid pressure decreasing component in fluid connection with said vortex chamber and said deceleration component.

12. The vortex system of claim 11, wherein said fluid pressure decreasing component includes a venturi.

13. The vortex system of claim 11, wherein said fluid pressure decreasing component includes a nozzle.

14. The vortex system of claim 9 wherein said deceleration component includes a chamber.

15. The vortex system of claim 9 wherein said apertures are arranged in rows and staggered columns in said chamber housing.

16. The vortex system of claim 9 wherein said apertures are arranged in one row in said chamber housing.

17. A method for nebulizing and/or vaporizing a liquid, comprising:

receiving pressurized gas;

drawing in and mixing said liquid with said pressurized gas using a venturi component with said received pressurized gas;

generating a vortical flow at a vortex, the vortex atomizing the pressurized gas;

further mixing said mixed liquid and gas in the vortex, wherein said mixed liquid and gas enter into said vortex through a plurality of tangential apertures in a chamber wall enclosing said vortex;

reducing pressure of said mixed liquid and gas exiting from said vortex using a nozzle component; and decelerating said mixed liquid and gas in a chamber component.

* * * * *